United States Patent
Pacetti et al.

(10) Patent No.: US 9,669,137 B2
(45) Date of Patent: Jun. 6, 2017

(54) MODIFIED POLYLACTIDE POLYMERS

(71) Applicant: Abbott Cardiovascular Systems Inc., Santa Clara, CA (US)

(72) Inventors: Stephen Pacetti, San Jose, CA (US); Fuh-Wei Tang, Temecula, CA (US); Xiao Ma, Santa Clara, CA (US); Ni Ding, San Jose, CA (US); Derek Mortisen, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/613,304

(22) Filed: Feb. 3, 2015

(65) Prior Publication Data

US 2015/0217028 A1   Aug. 6, 2015

Related U.S. Application Data

(60) Provisional application No. 61/935,823, filed on Feb. 4, 2014, provisional application No. 61/943,225, filed on Feb. 21, 2014.

(51) Int. Cl.

| | | |
|---|---|---|
| *A61F 2/82* | (2013.01) | |
| *A61K 47/48* | (2006.01) | |
| *A61L 31/06* | (2006.01) | |
| *A61L 31/10* | (2006.01) | |
| *A61L 31/14* | (2006.01) | |
| *C08G 63/91* | (2006.01) | |
| *A61L 2/08* | (2006.01) | |
| *B29C 71/04* | (2006.01) | |
| *C08G 63/08* | (2006.01) | |
| *B29B 13/08* | (2006.01) | |
| *B29C 35/08* | (2006.01) | |
| *A61F 2/91* | (2013.01) | |

(52) U.S. Cl.
CPC ............ *A61L 31/06* (2013.01); *A61F 2/82* (2013.01); *A61K 47/482* (2013.01); *A61L 2/087* (2013.01); *A61L 31/10* (2013.01); *A61L 31/148* (2013.01); *B29B 13/08* (2013.01); *B29C 71/04* (2013.01); *C08G 63/08* (2013.01); *C08G 63/912* (2013.01); *A61F 2/91* (2013.01); *A61F 2210/0004* (2013.01); *A61F 2240/001* (2013.01); *A61F 2250/0067* (2013.01); *A61L 2300/606* (2013.01); *B29C 2035/085* (2013.01); *B29C 2035/0827* (2013.01); *B29C 2035/0877* (2013.01)

(58) Field of Classification Search
CPC ........ A61F 2210/0004; A61F 2240/001; A61F 2250/0067; A61F 2/82; A61F 2/91
See application file for complete search history.

(56) References Cited

U.S. PATENT DOCUMENTS

| | | | | |
|---|---|---|---|---|
| 5,439,686 | A * | 8/1995 | Desai ...................... | A23L 1/296 424/451 |
| 2009/0276036 | A1* | 11/2009 | Nagura ................... | A61L 31/10 623/1.44 |
| 2010/0247668 | A1* | 9/2010 | Eliasof ............. | A61K 47/48192 424/501 |
| 2012/0285123 | A1 | 11/2012 | Wang et al. | |

FOREIGN PATENT DOCUMENTS

WO    2009/148581 A1 * 12/2009

OTHER PUBLICATIONS

Taluja et al. (Journal of Materials Chemistry, published 2007, pp. 4002-4014).*
Sugai et al. (ACS Macro Letters, Published Jul. 3, 2012, pp. 902-906).*
Karikari et al. (Biomacromolecules, Published 2007, pp. 302-308).*
Kitamura et al. (Macromolecules, Published 2007, pp. 509-517).*
Xu et al. (Journal of Microencapsulation, Published 2009, pp. 659-666).*
Knight et al. (Macromolecules, Published 2009, pp. 6596-6605).*
Matsuo et al. (Makromolekulare Chemie, vol. 152, pp. 203-215, Published 1972).*
International Search Report and Written Opinion for PCT/US2015/014330, mailed Apr. 7, 2015, 9 pgs.

* cited by examiner

*Primary Examiner* — Alma Pipic
(74) *Attorney, Agent, or Firm* — Squire Patton Boggs (US) LLP

(57) ABSTRACT

It is provided herein modified polylactide (PLA) polymers comprising biocompatibile functional group(s) on the polymers and methods of making and using the modified PLA polymers.

19 Claims, 7 Drawing Sheets

MODIFIED POLYLACTIDE POLYMERS

CROSS-REFERENCE

This application claims the benefits of U.S. Provisional Application No. 61/935,823 filed on Feb. 4, 2014 and U.S. Provisional Application No. 61/943,225 filed on Feb. 21, 2014, the teachings of which are incorporated by reference in their entirety.

FIELD OF THE INVENTION

The invention is directed to implantable medical devices, coatings for such medical devices, and materials and methods for manufacturing the same.

BACKGROUND OF THE INVENTION

Percutaneous transluminal coronary angioplasty (PTCA) is a common procedure for treating heart disease. A problem associated with PTCA includes the formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, a stent may be implanted in the lumen to maintain the vascular patency.

Stents are generally tubular-shaped devices which function to hold open or reinforce a segment of a blood vessel or other body lumen, such as a coronary artery, carotid artery, saphenous vein graft, or femoral artery. They also are suitable to support and hold back a dissected arterial lining that could occlude the body lumen, to stabilize plaque, or to support bioprosthetic valves. Stents are typically delivered to a target area within the body lumen using a catheter. A balloon-expandable stent is mounted to a balloon catheter, navigated to the appropriate area, and expanded by inflating the balloon. A self-expanding stent is delivered to the target area and released, expanding to the required diameter to treat the disease.

Stents are used not only as a mechanical intervention but also as a vehicle for providing biological or pharmaceutical therapy. As a mechanical intervention, stents act as scaffoldings, functioning to physically hold open and, if desired, to expand the wall of the passageway. Biological or pharmaceutical therapy can be achieved by medicating the stents, in particular by using drug-eluting stents, DESs. DESs can provide local administration of a therapeutic substance, such as a drug, a pharmaceutical agent, or a biologic at the specific site in a patient's body. This can result in fewer and less severe side effects and more favorable overall results.

Implantable medical devices such as stents can be formed from various materials, such as polymeric and/or metallic materials, and may be non-degradable or biodegradable. An implantable device can be fabricated with a coating containing partially or completely a biodegradable polymer, a biostable polymer, or a combination thereof. An implantable device body can be fabricated partially or completely from a biodegradable polymer, a biostable polymer, or a combination thereof.

Biodegradable polymers may degrade by hydrolysis and other reaction mechanisms in the vascular or other luminal environments over time. Usually, it will be desirable to have the stent or endoprosthesis completely degrade after it has served its needed supporting function in the body lumen. Typically, complete degradation will be desired in less than three years, sometime less than one year, or in a matter of months after implantation.

Polylactide (PLA) based polymers have been used to fabricate bioabsorbable implantable medical devices. Although PLA based polymers have been used widely in many lactide based drug delivery systems, the present inventors have found that modification of their chemical structure can broaden their application.

SUMMARY

It is provided herein a modified polylactide (PLA) polymer comprising biocompatible functional group(s) (BFG), wherein the BFG(s) is at one or both ends of the polymer backbone or in the polymer backbone.

In certain embodiments, the modified PLA polymer is produced by modifying a PLA polymer thereby generating BFG(s) on the PLA polymer, wherein the BFG(s) is at one or both ends of the polymer backbone or in the polymer backbone.

In certain embodiments, it is provided herein a method of modifying a PLA polymer to generate new BFG(s) in the polymer chain. In certain embodiments, the method comprises subjecting a PLA polymer to an energy treatment followed by exposing the energy treated PLA polymer to oxygen.

The modified PLA polymers or polymer blends comprising the modified PLA polymers are useful for bioabsorbable medical devices (e.g., stents) and/or coatings thereof. The modified PLA polymers can also react with a therapeutic agent, a diagnostic agent, a hydrophilic component, a hydrophobic component, or a combination thereof via the BFG(s) to broaden and enhance the applications of PLA polymers.

It is also provided a modified PLA polymer conjugate produced by reacting the BFG(s) of the modified PLA polymer described herein with a therapeutic agent, a diagnostic agent, a hydrophilic component, a hydrophobic component, or a combination thereof.

It is further provided a method of fabricating an implantable medical device, or coating for an implantable medical device which comprises a modified PLA polymer or a modified PLA polymer conjugate described herein.

It is further provided a method of treating, preventing, or diagnosing a condition or disorder using an implantable medical device described herein.

Figure 1:
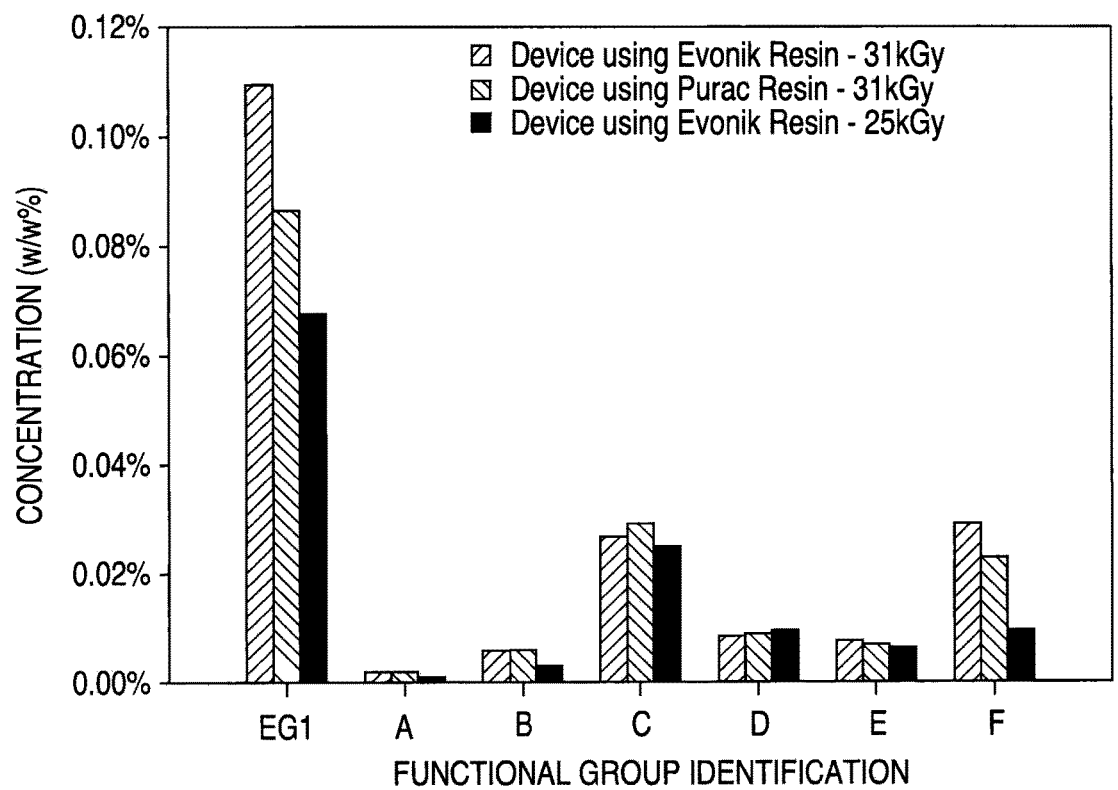
FIG. 1 shows quantification of peaks from device using Evonik PLLA Resins with 31 kGy e-beam, device using PURAC PLLA Resins with 31 kGy E-beam, and device using Evonik PLLA Resins with 25 kGy E-beam (left to right).

Biocompatible functional groups A-F are listed in Table 1 in the present specification.

DETAILED DESCRIPTION

Definition

It is understood that use of the singular throughout this application including the claims includes the plural and vice versa unless expressly stated otherwise. That is, "a" and "the" are to be construed as referring to one or more of whatever the word modifies. Non-limiting examples include: "a therapeutic agent" which is understood to include one such agent, two such agents or, under the right circumstances, as determined by those skilled in the treatment of diseased tissues, even more such agents unless it is expressly stated or is unambiguously obvious from the context that such is not intended. Likewise, "a bioabsorbable polymer" refers to a single polymer or a mixture of two or more polymers unless, again, it is expressly stated or absolutely obvious from the context that such is not intended.

As used herein, words of approximation, such as "about" or "approximately" when used to describe numerical values or ranges are understood to mean that those skilled in the art would readily consider a value different from the exact number or outside the actual range to be close enough to be within the protection sought of that number or range. At the very least, "about" or "approximately" is understood to mean±15% of a given numerical value or range starting and ending point.

As used herein, a "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a "therapeutic agent" also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded. As used herein, the term "therapeutic agent" is used interchangeably with the term "drug."

As used herein, a "diagnostic agent" refers to a chemical substance used to reveal, pinpoint, and define the localization of a pathological process.

As used herein, "treating" refers to the administration of a therapeutically effective amount of a therapeutic agent to a patient known or suspected to be suffering from a disease, such as a vascular disease.

As used herein, a "therapeutically effective amount" refers to that amount of a therapeutic agent that will have a beneficial effect, which may be curative or palliative, on the health and well-being of the patient with regard to the disease (e.g., vascular disease) with which the patient is known or suspected to be afflicted. A therapeutically effective amount may be administered as a single bolus, as intermittent bolus charges, or as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "subject" refers to any species that might benefit from treatment using the method herein but at present preferably a mammal and most preferably a human being.

As used herein, a "vascular disease" refers to a disease of the vessels, primarily arteries and veins, which transport blood to and from the heart, brain and peripheral organs such as, without limitation, the arms, legs, kidneys and liver. In particular, a "vascular disease" refers to a disease of the coronary arterial system, the carotid arterial system, and the peripheral arterial system. The disease that may be treated is any that is amenable to treatment with a therapeutic agent, either as the sole treatment protocol or as an adjunct to other procedures such as surgical intervention. The disease may be, without limitation, restenosis, thrombosis, atherosclerosis, vulnerable plaque, or peripheral arterial disease.

"Restenosis" refers to the re-narrowing or blockage of an artery at or near the site where angioplasty or another surgical procedure was previously performed to remove a stenosis. It is generally due to smooth muscle cell proliferation and, at times, is occasionally accompanied by thrombosis. Prior to the advent of implantable stents to maintain the patency of vessels opened by angioplasty, restenosis occurred in 40-50% of patients within 3 to 6 months of undergoing the angioplasty procedure. Post-angioplasty restenosis before stents was due primarily to vessel recoil. There were also issues of acute re-closure due to vasospasm, dissection, and thrombosis at the site of the procedure. Stents eliminates acute closure from vasospasm and vessel recoil and greatly reduces complications from dissections. Stent placement sites are susceptible to restenosis due to abnormal tissue growth at the site of implantation. Restenosis tends to occur in 3 to 6 months after stent placement but it is not affected by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time and have effectively reduced restenosis.

"Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to the brain, it causes a stroke.

"Atherosclerosis" refers to the depositing of fatty substances, cholesterol, cellular waste products, calcium, and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ from the particular artery is depleted. Consequently, it causes strokes, if the afflicted artery is a carotid artery, heart attack if the artery is a coronary artery, or loss of organ function if the artery supplies blood to that organ.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque with tissue factor is exposed to blood, with the potential of causing a potentially fatal thrombotic event through adhesion and activation of platelets and plasma proteins to components of the exposed plaque. The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth in the arterial wall. The intrinsic histological features that may characterize a vulnerable plaque include increased lipid content, increased macrophage, foam cell and T lymphocyte content, and reduced collagen and smooth muscle cell (SMC) content.

As used herein, and unless otherwise specified, the terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked, and any other variations of polymers. The terms are inclusive of a polymer blend of two or more polymers, for example, three, four, five, six, seven, eight, nine, and ten polymers. The polymers in the blend can be of various ratios. For example, in a two polymer blend, the amount of one polymer can vary from 0.5% to 99.5% by weight, and the other polymer can vary from 99.5% to 0.5% by weight.

As used herein, a "polylactide polymer" or "PLA polymer" refers to a homopolymer of lactide or a copolymer of lactide with one or more other monomers, i.e., a PLA copolymer. As used herein, the term "PLA polymer" may be used interchangeably with the term "PLA based polymer." A PLA polymer can be formed from D-lactide or D-lactic acid, L-lactide or L-lactic acid, D,L-lactide, meso-lactide, racemic mixture of D- and L-lactide- or combination thereof. The content of lactide in the PLA copolymer is at least 5% by weight, for example at least 10%, 15%, 20%, 25%, 30%, 35%, 40%, 45%, 50%, 55%, 60%, 65%, 70%, 75%, 80%, 85%, 90%, or 95% by weight. A polylactide copolymer, unless otherwise specified, can include an alternating copolymer, a periodic copolymer, a statistical copolymer, a random copolymer, a block copolymer, a graft copolymer, a crosslinked copolymer, and/or a stereoblock copolymer. A PLA copolymer can include, unless otherwise specified, two, three, four, or more different types of repeating monomer, oligomer, and/or polymer units. The block copolymer can have two, three, four, or more blocks. In certain embodiments, each block comprises or is formed of one type of monomer.

As used herein, the terms "bioabsorbable," "bioresorbable" "bioerodable," and "biodegradable" can be used interchangeably. By "bioabsorbable" or "bioresorbable," it is meant that a polymer, a polymeric scaffold, a polymeric substrate, or a polymeric coating can, for example, be absorbed by a subject's body. By "biodegradable," it is meant that a polymer, a polymeric scaffold, a polymeric substrate, or a polymeric coating can be disposed of in a subject's body. Biodegradation occurs through hydrolysis, enzymatic reactions, oxidation, and other chemical reactions. Bioabsorption or biodegradation can take place over a relatively short period of time, for example, 1-6 months, or an extended period of time, for example over 6 months, under physiological conditions.

As used herein, a biostable polymer or coating refers to a polymer or coating that is not biodegradable, which is defined above. The term "biostable" is used interchangeably with the term "non-degradable".

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH, and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

As used herein, the molecular weight of a polymer refers to average molecular weight. Polymer molecular weights are usually given as averages. Two experimentally determined values are common: $M_n$, the number average molecular weight, and $M_w$, the weight average molecular weight. $M_n$ is calculated from the mole fraction distribution of different sized molecules in a sample, and $M_w$ is calculated from the weight fraction distribution of different sized molecules. Unless otherwise specified, the molecular weight of a polymer as used herein refers to the weight average molecular weight $M_w$.

Modified Polylactide Polymer and Method of Making

Depending on the application, there may be a need to modify the existing PLA polymer to introduce biocompatible functional group(s) (BFG) into the polymer chain. The PLA polymer can be either PLA homopolymer or PLA copolymer. Reactions of a therapeutic agent, a diagnostic agent, a hydrophilic, a hydrophobic component, or a combination thereof with the BFG(s) in the modified PLA polymers can broaden and enhance the applications of PLA polymers.

Thus it is provided herein a method of modifying a PLA polymer to generate BFG(s) in the polymer chain. The modified PLA polymers or polymer blends comprising the modified PLA polymers are useful for making bioabsorbable medical devices (e.g., stents) and/or coatings thereof.

In certain embodiments, the method comprises subjecting a PLA polymer to an energy treatment followed by exposing the energy treated PLA polymer to oxygen. In certain embodiments, the method comprises subjecting a polymer blend comprising a PLA polymer to an energy treatment followed by exposing the energy treated PLA polymer to oxygen.

Energy treatments include, but are not limited by, electron beam (e-beam) irradiation, gamma irradiation, UV irradiation, plasma sterilization, peroxide sterilization, elevated dry heat, chlorine dioxide, or ozone. Exposing to oxygen can be done by exposing to air comprising certain amount of oxygen.

In certain embodiments, the energy treatment is e-beam. Exposure of a PLA polymer to e-beam (e.g., 10-100 kGy) reduces the molecular weight of the PLA polymer and generates many functional groups to the polymer. Furthermore, the amount of each individual functional group can be modulated by variation of e-beam dose, e-beam environment, and/or addition of antioxidant, hydrogen extractable chemical, or hydrogen donor species.

In certain embodiments, the medical device is packaged under inert gases, such as nitrogen or argon (i.e., normal condition). In certain embodiments, the medical device is packaged under nitrogen with certain amount of hydrogen ($H_2$). The amount of $H_2$ can be from 0.1% to 99.9%, for example 1%. In certain embodiments, the medical device is packaged under nitrogen with certain amount of isopropyl alcohol (IPA). The amount of IPA can be from 0.5% to 10%, for example 4.3%. In certain embodiments, the medical device is packaged under air containing certain amount of oxygen ($O_2$). The amount of $O_2$ can be from 0.5% to 99.9%, for example 21%.

In certain embodiments, the e-beam dose is between about 5 kGy to about 100 kGy. In certain embodiments, the e-beam dose is about 5 kGy. In certain embodiments, the e-beam dose is about 10 kGy. In certain embodiments, the e-beam dose is about 25 kGy. In certain embodiments, the E-beam dose is about 31 kGy.

In certain embodiments, the E-beam dose can be applied once, twice, or more times.

In certain embodiment, antioxidant such as butylated hydroxytoluene (BHT), polyphenol (BHA), thiol containing compounds (e.g., N-acetylcysteine, bucillamine), and natural vitamins (C and E) can be included on the top of the scaffold or within the package. Antioxidant can also be blended with polymer. In certain embodiments, the amount of antioxidant mixed in the polymeric device ranges from 0.05% to 5% by weight.

All organic molecules containing extractable hydrogen with relatively high vapor pressure can be included in the package to modify the polymer structure upon radiation exposure. Non-exclusive examples of these molecules are methane, ethane, propane, and butanone, The PLA polymers include, but are not limited to, poly (L-lactide), poly(D-lactide), poly(D,L-lactide), poly(L-lactide-co-D,L-lactide), poly(D-lactide-co-D,L-lactide), poly (L-lactide-co-glycolide), poly(D-lactide-co-glycolide), poly (L-lactide-co-caprolactone), poly(D-lactide-co-caprolactone), poly(L-lactide-co-trimethylene carbonate), poly(D-lactide-co-trimethylene carbonate), poly(D,L-lactide-co-glycolide), poly(D,L-lactide-co-caprolactone), poly (D,L-lactide-co-trimethylene carbonate), and their respective blends. The copolymer can be block copolymer or random copolymer. After E-beam, new functional groups are formed on the PLA polymers.

For example, E-beam irradiation of poly(L-lactide) (PLLA) generates the biocompatible functional groups listed in Table 1 described in EXAMPLE 1. PLA polymers containing other monomers generate unique end groups, which in some cases, are different from those in Table 1. Two exemplary PLA copolymers are poly(D,L-lactide-co-glycolide) (PDLLA-GA) and poly(L-lactide-co-glycolide) (PLLA-GA).

Polymer end groups formed when a PLA polymer containing glycolide is radiation sterilized include, but are not limited to,

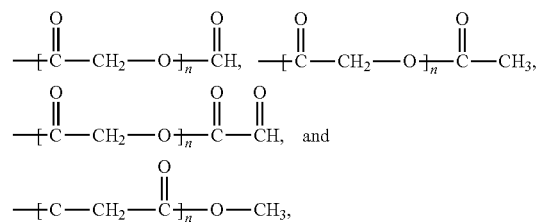

wherein n is an integer. In certain embodiments, n is a positive integer ranging from about 10 to about 10,000. In certain embodiments, n is a positive integer ranging from about 20 to about 5,000.

Another PLA polymer useful for fabricating a bioabsorbable stent scaffold or a coating is PLA copolymer containing ε-caprolactone. Introduction of ε-caprolactone into a PLA polymer creates a number of different groups both as end groups and groups in the polymer backbone following radiation sterilization. Polymer moieties with new end groups formed when a PLA copolymer containing ε-caprolactone is radiation sterilized include, but are not limited to,

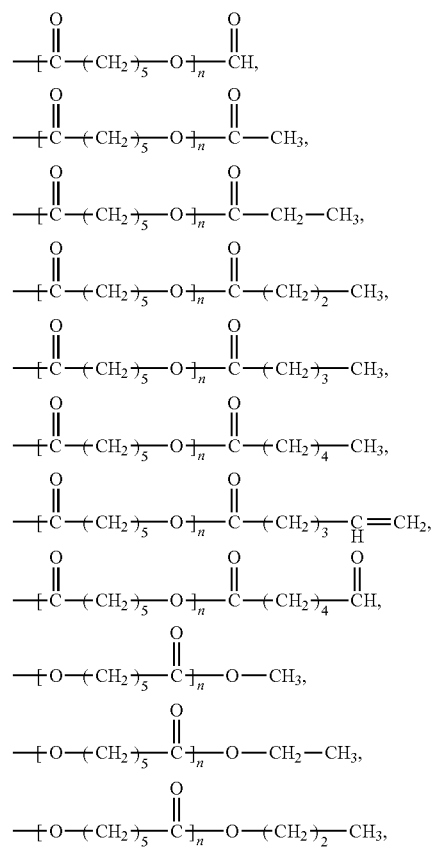

-continued

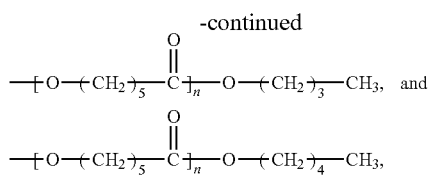

wherein m and n are independently a positive integer. In certain embodiments, n is independently a positive integer ranging from about 10 to about 10,000. In certain embodiments, n is independently a positive integer ranging from about 20 to about 5,000.

After E-beam treatment, new functional groups can form in the backbone of a PLA copolymer containing ε-caprolactone. For example, modified PLA copolymers containing ε-caprolactone can comprise moieties including, but not limited to

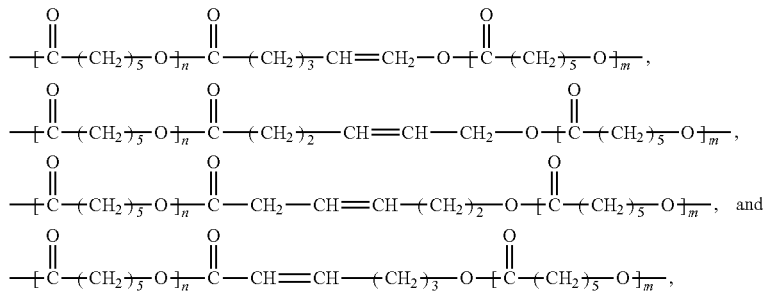

wherein m and n are independently a positive integer. In certain embodiments, m and n are independently a positive integer ranging from about 10 to about 10,000. In certain embodiments, m and n are independently a positive integer ranging from about 20 to about 5,000.

After E-beam treatment, new functional groups can form on both ends of these polymers. For example, modified poly(lactide-co-glycolide) polymers having two end groups include, but are not limited to

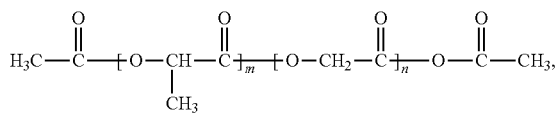

wherein m and n are independently a positive integer. In certain embodiments, m and n are independently a positive integer ranging from about 10 to about 10,000. In certain embodiments, m and n are independently a positive integer ranging from about 20 to about 5,000.

For another example, modified poly(lactide-co-caprolactone) polymers having two end groups include, but are not limited to

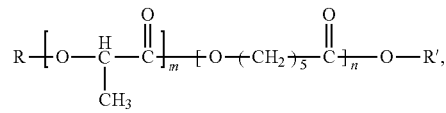

wherein m and n are independently positive integer; and wherein
R is —H, —CH$_3$, —CH$_2$CH$_3$, —CH=CH$_2$, —CH=CH$_2$CH$_3$,

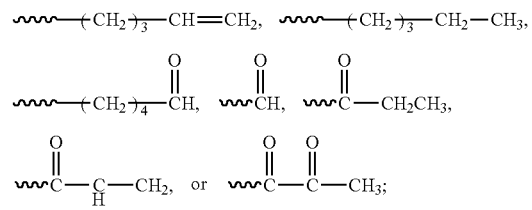

R' is —H, —CH$_3$, —CH$_2$CH$_3$, —CH=CH$_2$, —CH=CH$_2$CH$_3$,

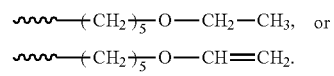

Thus, modified poly(lactide-co-caprolactone) polymers having two end groups include, but are not limited to

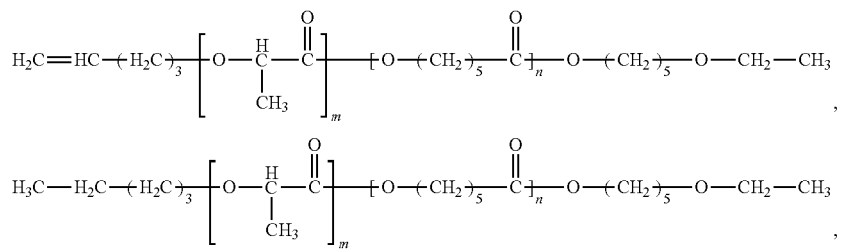

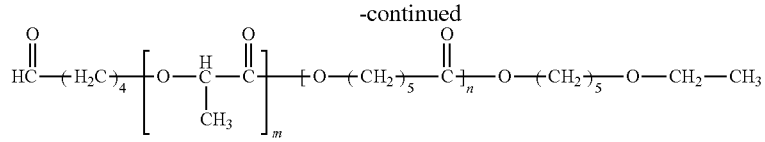

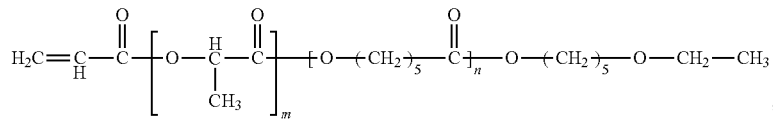

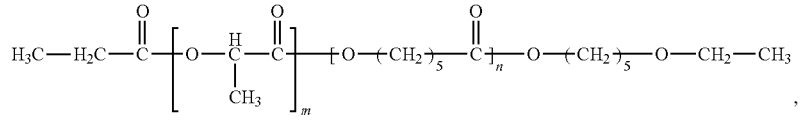

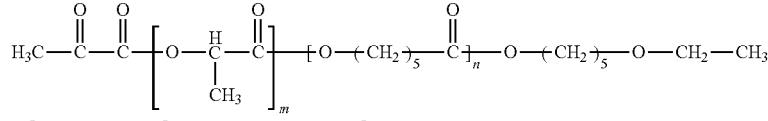

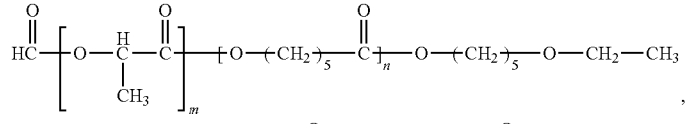

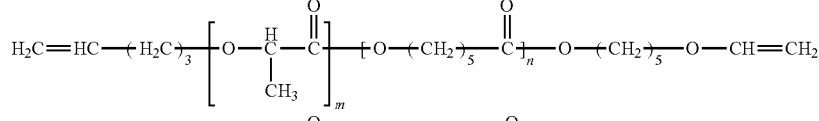

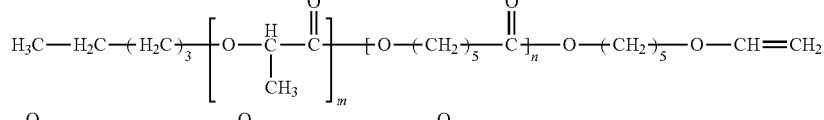

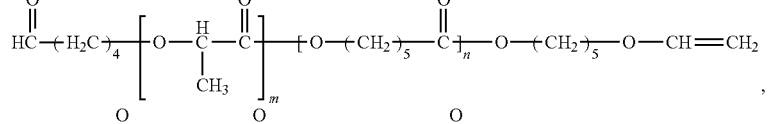

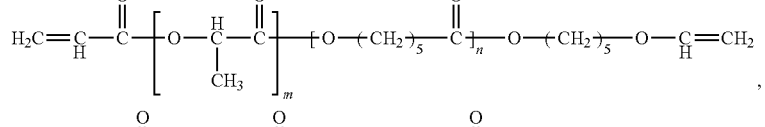

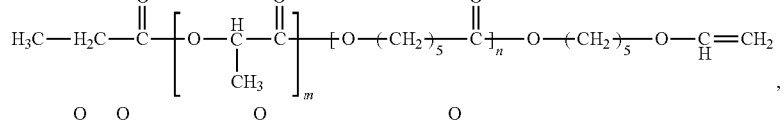

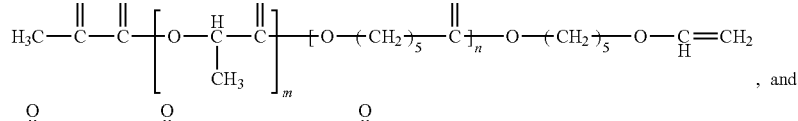

, and

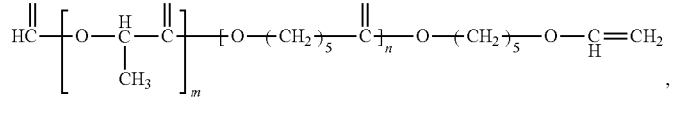

, wherein m and n are independently a positive integer. In certain embodiments, m and n are independently a positive integer ranging from about 10 to about 10,000. In certain embodiments, m and n are independently a positive integer ranging from about 20 to about 5,000.

For another example, modified poly(lactide-co-caprolactone) polymers having two end groups include, but are not limited to

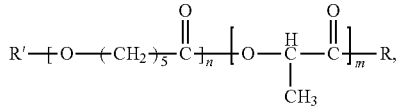

wherein m and n are independently positive integer, and wherein
R is —H, —CH₃, —CH₂CH₃, —CH=CH₂, —CH=CH₂CH₃,

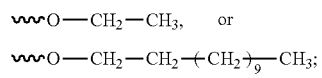

R' is —H, —CH₃, —CH₂CH₃, —CH=CH₂, —CH=CH₂CH₃,

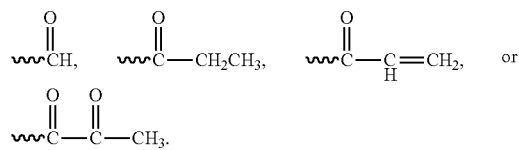

Thus, modified poly(lactide-co-caprolactone) polymers having two end groups include, but are not limited to,

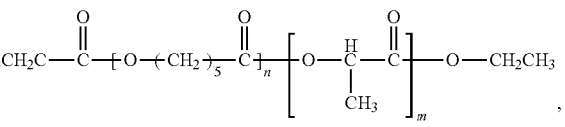

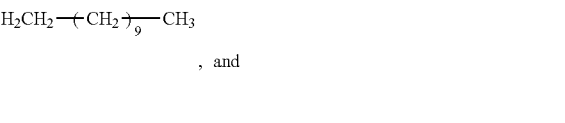

wherein m and n are independently a positive integer. In certain embodiments, m and n are independently a positive integer ranging from about 10 to about 10,000. In certain embodiments, m and n are independently a positive integer ranging from about 20 to about 5,000.

After e-beam treatment, new functional groups can form in the backbone of PLA polymers. For example, modified PLA polymers can comprise a moiety including, but not limited to

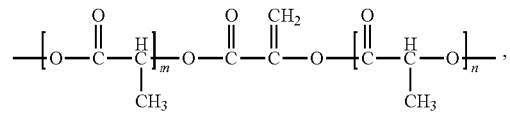

wherein m and n are independently positive integer. In certain embodiments, m and n are independently a positive integer ranging from about 10 to about 10,000. In certain embodiments, m and n are independently a positive integer ranging from about 20 to about 5,000.

It is provided herein a modified polylactide polymer comprising biocompatible functional group(s) (BFG), wherein the BFG(s) is at one or both ends of the polymer backbone or in the polymer backbone. When being in the polymer backbone, the BFG is not a pendant group.

In certain embodiments, the modified polylactide polymer is produced by modifying a polylactide polymer thereby generating BFG(s) in the polylactide polymer, wherein the BFG(s) is at one or both ends of the polymer backbone or in the polymer backbone.

In certain embodiments, the polylactide polymer is a homopolymer of lactide. The homopolymer is polymerized from D-lactide or D-lactic acid, L-lactide or L-lactic acid, D,L-lactide, or any combination thereof.

In certain embodiments, the polylactide polymer is a copolymer of lactide with one or more other monomers. In certain embodiments, the one or more other monomers are hydroxy alkanoate monomers or lactone monomers. Suitable hydroxy alkanoate monomers include, but are not limited to, glycolic acid or glycolide, 3-hydroxypropanoate, 3-hydroxybutyrate, 3-hydroxyvalerate, 3-hydroxyhexanoate, 3-hydroxyheptanoate, 3-hydroxyoctanoate, 4-hydroxybutyrate, 4-hydroxyvalerate, 4-hydroxyhexanote, 4-hydroxyheptanoate, and 4-hydroxyoctanoate. Suitable lactone monomers include, but are not limited to, α-acetolactone, β-propiolactone, γ-butyrolactone, δ-valerolactone, and ε-caprolactone. In certain embodiments, the PLA polymer comprises ε-caprolactone.

In certain embodiments, the polylactide polymer is selected from poly(L-lactide), poly(D-lactide), poly(D,L-lactide), poly(L-lactide-co-D,L-lactide), poly(D-lactide-co-D,L-lactide), poly(L-lactide-co-glycolide), poly(D-lactide-co-glycolide), poly(L-lactide-co-caprolactone), poly(D-lactide-co-caprolactone), poly(L-lactide-co-trimethylene carbonate), poly(D-lactide-co-trimethylene carbonate), poly(D,L-lactide-co-glycolide), poly(D,L-lactide-co-caprolactone), poly(D,L-lactide-co-trimethylene carbonate), and any combination or blend thereof.

In certain embodiments, the polylactide copolymer is a random copolymer. In certain embodiments, the polylactide copolymer is a block copolymer. The types of block copolymer include, but not limited to, AB, ABA, and BAB block polymers having blocks such as poly(L-lactide), poly(D-lactide), poly(D,L-lactide), polyglycolide, polycaprolactone, and poly(trimethylene carbonate). A block can be a polymer or oligomer of one monomer, or a polymer or oligomer of two or more monomers.

In certain embodiments, it is provides a blend of polymers. The blend can be a blend of two or more polymers, for example, three, four, five, six, seven, eight, nine, and ten polymers. The blend comprises at least one modified polylactide polymer described herein. In certain embodiments, the blend can be any combination of polylactide polymer(s) and modified polylactide polymer(s) described herein. In certain embodiments, the blend further comprises a non-polylactide polymer described herein. In certain embodiments, a blend of poly(L-lactide) and poly(L-lactide-co-caprolactone) with either or both modified as described herein is used, optionally with a non-polylactide polymer. Each polymer in the blend can be of various ratios. For example, in a two polymer blend, the amount of one polymer can vary from 0.5% to 99.5% by weight, and the other polymer can vary from 99.5% to 0.5% by weight.

In certain embodiments, the polylactide polymer has a molecular weight ranging from about 2,000 Daltons to about 2,000,000 Daltons. In certain embodiments, the polylactide polymer has a molecular weight ranging from about 10,000 Daltons to about 1,000,000 Daltons. For example, the polylactide polymer has a molecular weight of about 10,000 Daltons, about 20,000 Daltons, about 30,000 Daltons, about 40,000 Daltons, about 50,000 Daltons, about 100,000 Daltons, about 150,000 Daltons, about 250,000 Daltons, about 350,000 Daltons, about 450,000 Daltons, about 500,000 Daltons, about 600,000 Daltons, about 700,000 Daltons, about 800,000 Daltons, about 900,000 Daltons, about 1,000,000 Daltons, about 1,500,000 Daltons, about 2,000,000 Daltons; or in any range between any two of these numbers, e.g., between 10,000 Daltons and 20,000 Daltons, between 30,000 Daltons and 50,000 Daltons, between 50,000 Daltons and 150,000 Daltons, between 250,000 Daltons and 1,000,000 Daltons, and so on.

In certain embodiments, the polylactide polymer is a copolymer wherein monomer lactide constitutes, about 1% to about 99% by weight of the copolymer. For example, lactide constitutes, by weight, about 1%, about 2%, about 3%, about 4%, about 5%, about 10%, about 20%, about 30%, about 40%, about 50%, about 60%, about 70%, about 80%, about 90%, about 95%, about 99% by weight of the copolymer, or any range between these numbers, e.g., between 5% and 10%, between 10% and 20%, between 20% and 30%, and so on. In certain embodiments, the content of lactide in the PLA copolymer is at least 5% by weight, for example at least 5%, 10%, 15%, 20%, 25%, 30%, 35%, 40%, 45%, 50%, 55%, 60%, 65%, 70%, 75%, 80%, 85%, 90%, or 95% by weight.

In certain embodiments, a polylactide polymer is modified to have a biocompatible functional group at one end of the polymer. In certain embodiments, a polylactide polymer is modified to have two biocompatible functional groups, one at each end of the polymer. In certain embodiments, a polylactide polymer is modified to have a biocompatible functional group in the polymer backbone. In certain embodiments, a polylactide polymer is modified to have biocompatible functional group(s) at the end(s) of the polymer as well as in the polymer backbone.

Thus, the modified polylactide polymers include, but are not limited to, one of the following structures:

BFG1-polylactide polymer-BFG2, polylactide polymer-BFG3-polylactide polymer,

BFG1-polylactide polymer-BFG3-polylactide polymer-BFG2,

BFG1-polylactide polymer-BFG3-polylactide polymer, polylactide polymer-BFG3-polylactide polymer-BFG2;

BFG1 and BFG2 can be same or different. BFG1 and BFG2 are also referred to as "end group" or "terminal group" because they are located at the ends of the polymer.

When any end of the modified polylactide polymer is not modified, it has the end group that is resulted from the polymerization of the monomer(s) that forms the repeating unit(s) of the polymer using polymerization methods known in the art.

Exemplary BFG1 and BFG2 groups include, but are not limited to —H, —CH$_3$, —CH$_2$CH$_3$, —CH=CH$_2$, —CH=CH$_2$CH$_3$,

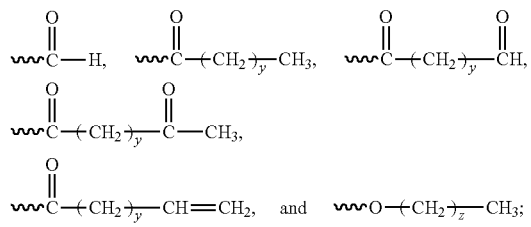

wherein y is an integer ranging from 0 to 4 inclusive, z is an integer ranging from 0 to 15 inclusive. In various embodiments, y is 0, 1, 2, 3, or 4. In various embodiments, z is an integer ranging from 0 to 11 or 0 to 4. In various embodiments, z is 0, 1, 2, 3, 4, or 11.

Exemplary BFG3 groups include, but are not limited to, a group according to any one of

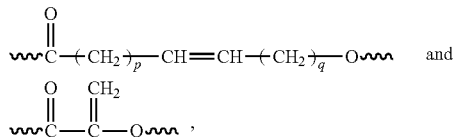

and

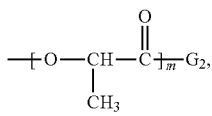

wherein p is an integer ranging from 0 to 3 inclusive, q is an integer ranging from 3 to 0 inclusive, provided p+q=3. In various embodiments, p is 0, q is 3; p is 1, q is 2; or p is 2, q is 1.

In certain embodiments, the modified PLA polymer comprises a moiety of any one of following formulae:

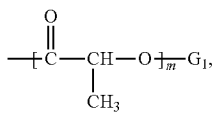   (I)

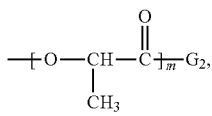   (II)

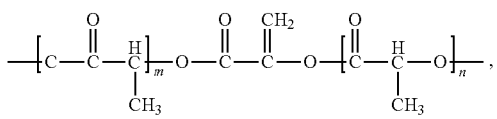   (III)

wherein
m and n are independently a positive integer, and
$G_1$ and $G_2$ are independently the new biocompatible functional group (BFG). In certain embodiments, m and n are independently a positive integer ranging from about 10 to about 10,000. In certain embodiments, m and n are independently a positive integer ranging from about 20 to about 5,000

$G_1$ groups include, but are not limited to —H, —$CH_3$, —$CH_2CH_3$, —CH=$CH_2$, —CH=$CH_2CH_3$,

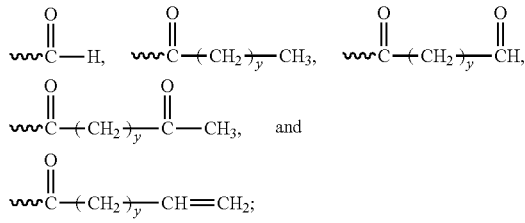

wherein y is an integer ranging from 0 to 4 inclusive. In various embodiments, y is 0, 1, 2, 3, or 4.

$G_2$ groups include, but are not limited to —H, —$CH_3$, —$CH_2CH_3$, —CH=$CH_2$, —CH=$CH_2CH_3$,

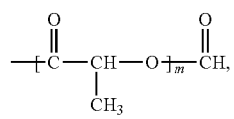

wherein z is an integer ranging from 0 to 15 inclusive. In various embodiments, z is an integer ranging from 0 to 11 or 0 to 4. In various embodiments, z is 0, 1, 2, 3, 4, or 11.

In certain embodiments, the modified polylactide polymer comprises a moiety including, but are not limited to

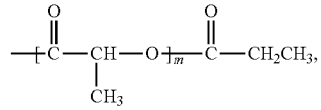

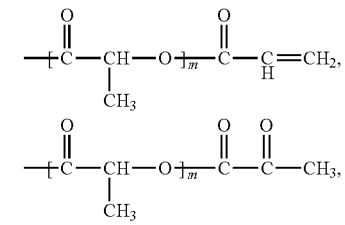

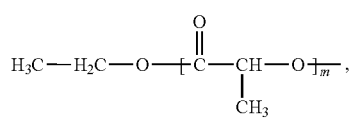

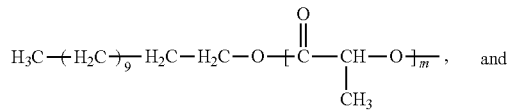

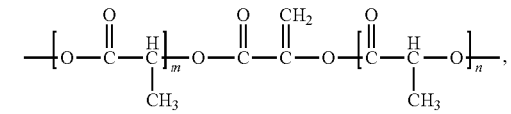

wherein m and n are independently a positive integer. In certain embodiments, m and n are independently a positive integer ranging from about 10 to about 10,000. In certain embodiments, m and n are independently a positive integer ranging from about 20 to about 5,000.

In certain embodiments, the polylactide polymer is a homopolymer polymerized from L-lactide or L-lactic acid, D-lactide or D-lactic acid, D,L-lactide, meso-lactide, or combination thereof. In such embodiments, the modified polylactide polymer can be of Formula (I) or (II) with the other end capped with a group as the result of polymerization. For example, the other end of Formula (I) can be capped with a hydroxyl group, and the other end of Formula (II) can be capped with a hydrogen. The modified polylactide polymer can be of formula (III) with both ends capped with a group as the result of polymerization. For example, both ends of Formula (III) can be capped with hydrogen.

In certain embodiments, the modified polylactide polymer comprises a moiety of any one of the following formulae:

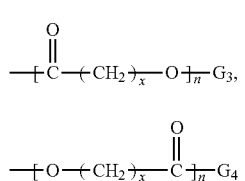

(IV)

(V)

wherein n is a positive integer, x is an integer ranging from 1 to 5 inclusive; and $G_3$ and $G_4$ are independently the new biocompatible functional group (BFG). In certain embodiments, n is a positive integer ranging from about 10 to about 10,000. In certain embodiments, n is a positive integer ranging from about 20 to about 5,000.

In certain embodiments, the modified polylactide polymer comprises a moiety of any one of the following formulae:

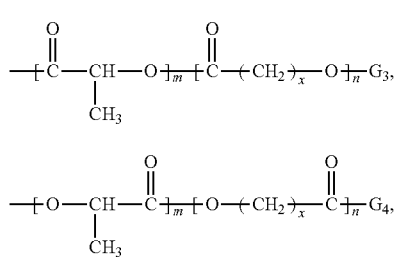

(VI)

(VII)

wherein m and n are independently a positive integer, x is an integer ranging from 1 to 5 inclusive; and $G_3$ and $G_4$ are independently the biocompatible functional group. In certain embodiments, m and n are independently a positive integer ranging from about 10 to about 10,000. In certain embodiments, m and n are independently a positive integer ranging from about 20 to about 5,000.

In certain embodiments, the polylactide polymer is a copolymer of lactide with at least one other monomer which is glycolide or ε-caprolactone, thus x in Formulae (IV) to (VII) is 1 or 5 respectively.

$G_3$ group includes, but is not limited to —H, —CH$_3$, —CH$_2$CH$_3$, —CH=CH$_2$, —CH=CH$_2$CH$_3$,

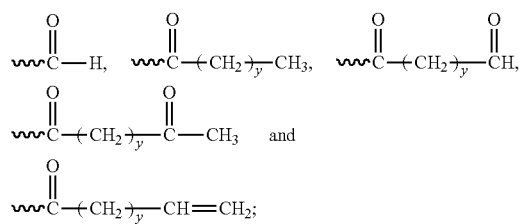

wherein y is an integer ranging from 0 to 4 inclusive.

$G_4$ group includes, but is not limited to —H, —CH$_3$, —CH$_2$CH$_3$, —CH=CH$_2$, —CH=CH$_2$CH$_3$,

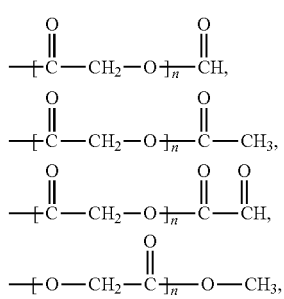

wherein z is an integer ranging from 0 to 15 inclusive. In various embodiments, z is an integer ranging from 0 to 11 or 0 to 4. In various embodiments, z is 0, 1, 2, 3, 4, or 11.

In certain embodiments, the polylactide polymer contains glycolide; and the modified polylactide polymer comprises a moiety of any one of the following formulae:

wherein n is a positive integer. In certain embodiments, n is a positive integer ranging from about 10 to about 10,000. In certain embodiments, n is a positive integer ranging from about 20 to about 5,000.

In certain embodiments, the polylactide polymer contains ε-caprolactone; and the modified polylactide polymer comprises a structure of any one of the following formulae:

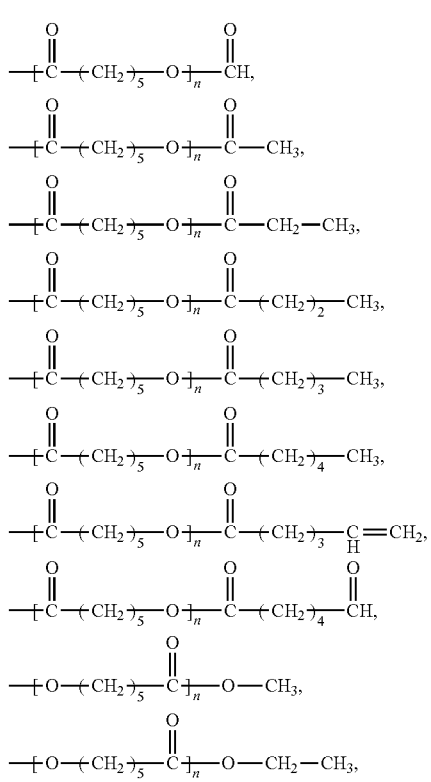

-continued

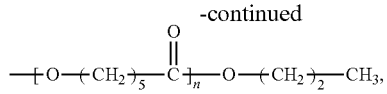

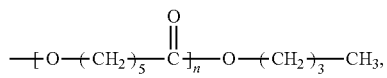

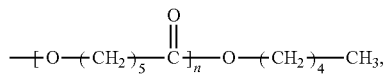

wherein n is a positive integer. In certain embodiments, n is a positive integer ranging from about 10 to about 10,000. In certain embodiments, n is a positive integer ranging from about 20 to about 5,000.

In certain embodiments, the modified polylactide polymer comprises a moeity of any one of the following formulae:

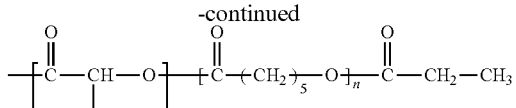

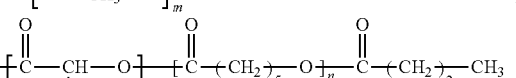

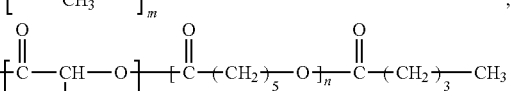

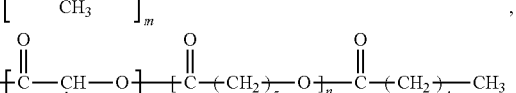

-continued

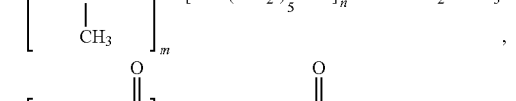

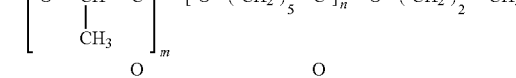

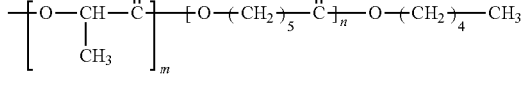

wherein m and n are independently a positive integer. In certain embodiments, m and n are independently a positive integer ranging from about 10 to about 10,000. In certain embodiments, m and n are independently a positive integer ranging from about 20 to about 5,000.

In certain embodiments, the modified polymer has a biocompatible functional group in the polymer backbone and comprises a structure of the following formula:

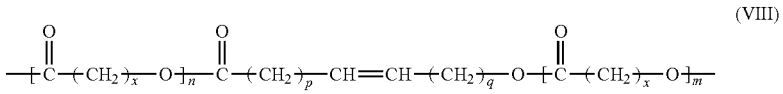

(VIII)

wherein
m and n are independently a positive integer,
x is an integer ranging from 1 to 5 inclusive,
p is an integer ranging from 0 to 3 inclusive, q is an integer ranging from 3 to 0, provided p+q=3. In certain embodiments, m and n are independently a positive integer ranging from about 10 to about 1000. In certain embodiments, m and n are independently a positive integer ranging from about 20 to about 5,000.

In certain embodiments, the polylactide polymer is copolymer of lactide and ε-caprolactone, which comprises, as part of the copolymer, a moiety of any one of the following formulae:

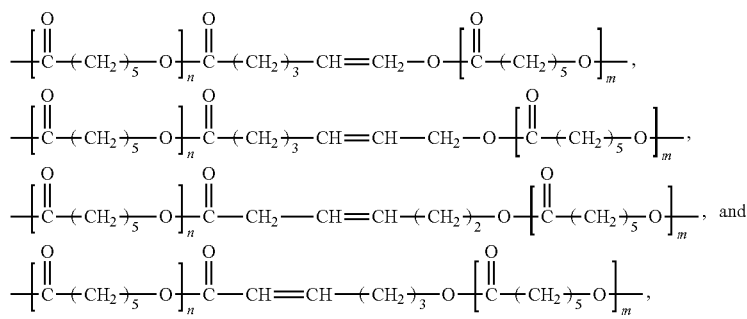

wherein m and n are dependently a positive integer. In certain embodiments, m and n are independently a positive integer ranging from about 10 to about 10,000. In certain embodiments, m and n are independently a positive integer ranging from about 20 to about 5,000.

In certain embodiments, the modified polymer has two biocompatible functional end groups and is of the following formula:

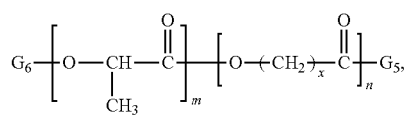

(IX)

wherein m and n are independently a positive integer; x is an integer ranging from 1 to 5 inclusive; and $G_5$ and $G_6$ are the biocompatible functional groups. In certain embodiments, m and n are independently a positive integer ranging from about 10 to about 10,000. In certain embodiments, m and n are independently a positive integer ranging from about 20 to about 5,000.

In certain embodiments, the polylactide polymer is a copolymer of lactide and at least one other monomer which is glycolide or ε-caprolactone; thus x in Formula (IX) is 1 or 5.

$G_5$ group includes, but is not limited to —H, —CH$_3$, —CH$_2$CH$_3$, —CH=CH$_2$, —CH=CH$_2$CH$_3$,

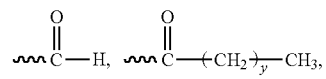

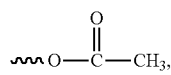

wherein z is an integer ranging from 0 to 15 inclusive. In various embodiments, z is an integer ranging from 0 to 11 or 0 to 4. In various embodiments, z is 0, 1, 2, 3, 4, or 11.

$G_6$ includes, but is not limited to —H, —CH$_3$, —CH$_2$CH$_3$, —CH=CH$_2$, —CH=CH$_2$CH$_3$,

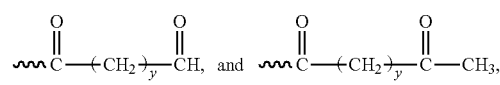

-continued

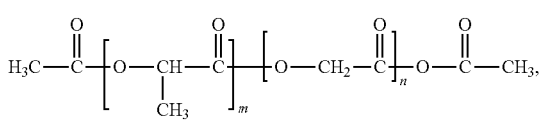

wherein y is an integer ranging from 0 to 4 inclusive.

In certain embodiments, the modified PLA polymer is a poly(lactide-co-glycolide) having two end groups of the following formula:

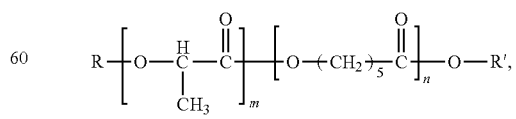

wherein m and n are independently a positive integer. In certain embodiments, m and n are independently a positive integer ranging from about 10 to about 10,000. In certain embodiments, m and n are independently a positive integer ranging from about 20 to about 5,000.

In certain embodiments, the modified PLA polymer is a modified poly(lactide-co-caprolactone) having two end groups of the following Formula:

$$R\!\!-\!\!\left[\!O\!-\!\overset{H}{\underset{CH_3}{C}}\!-\!\overset{O}{\overset{\|}{C}}\right]_m\!\!\left[\!O\!\!-\!\!(CH_2)_5\!\!-\!\!\overset{O}{\overset{\|}{C}}\right]_n\!\!\!-\!O\!-\!R',$$

wherein m and n are independently a positive integer,
R is —H, —CH$_3$, —CH$_2$CH$_3$, —CH=CH$_2$, —CH=CH$_2$CH$_3$,

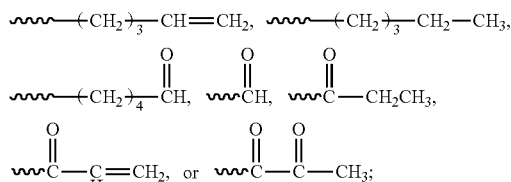
R' is —H, —CH$_3$, —CH$_2$CH$_3$, —CH=CH$_2$, —CH=CH$_2$CH$_3$,
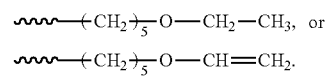
In certain embodiments, m and n are independently a positive integer ranging from about 10 to about 10,000. In certain embodiments, m and n are independently a positive integer ranging from about 20 to about 5,000.
Thus, modified poly(lactide-co-caprolactone) polymers having two end groups include, but are not limited to,
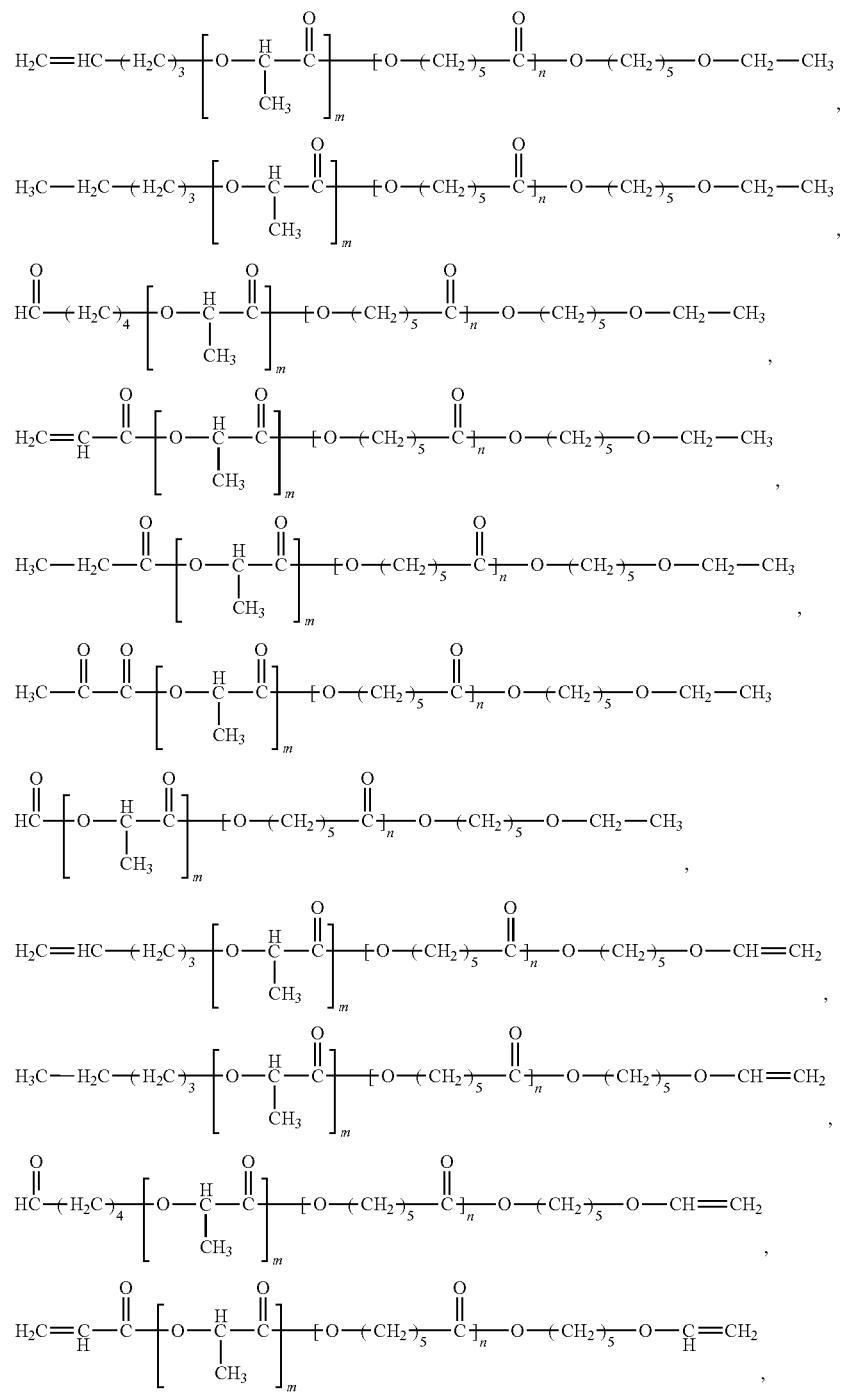

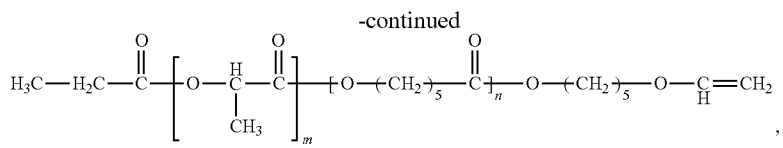

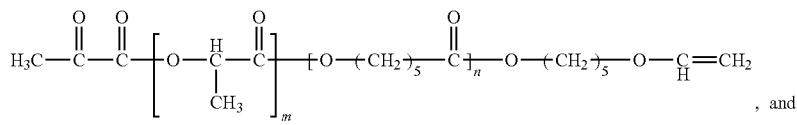

, and

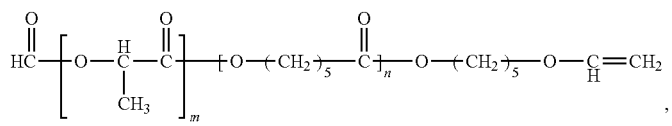

, wherein m and n are independently a positive integer.

In certain embodiments, the modified PLA polymer is a modified poly(lactide-co-caprolactone) polymers having two end groups, including, but not limited to,

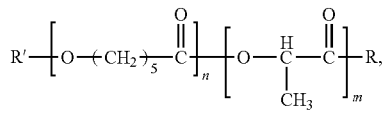

wherein m and n are independently positive integer, and wherein

R is —H, —CH$_3$, —CH$_2$CH$_3$, —CH=CH$_2$, —CH=CH$_2$CH$_3$,

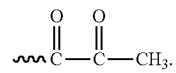

R' is —H, —CH$_3$, —CH$_2$CH$_3$, —CH=CH$_2$, —CH=CH$_2$CH$_3$,

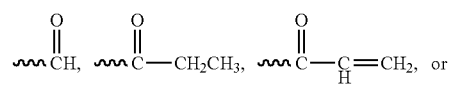

In certain embodiments, m and n are independently a positive integer ranging from about 10 to about 10,000. In certain embodiments, m and n are independently a positive integer ranging from about 20 to about 5,000.

Thus, modified poly(lactide-co-caprolactone) polymers having two end groups include, but are not limited to,

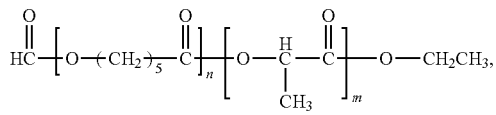

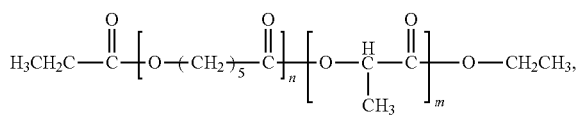

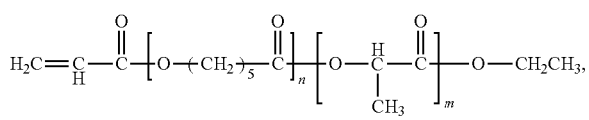

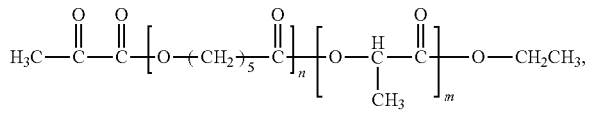

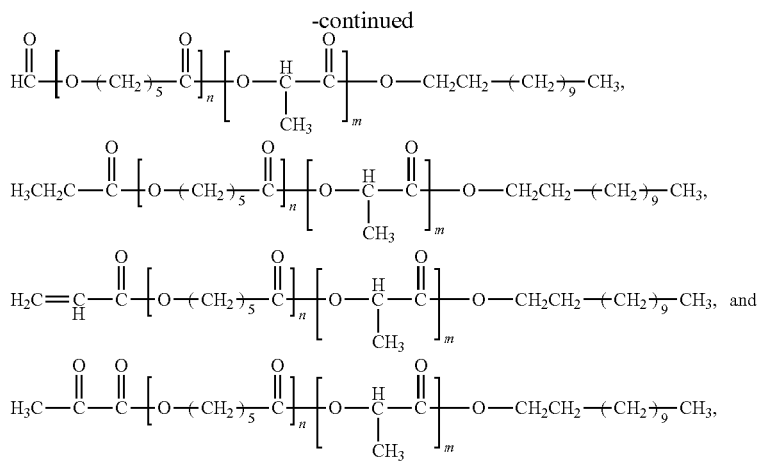

wherein m and n are independently a positive integer.

Modified Polylactide Polymer Conjugate

It is provided herein a modified polylactide polymer conjugate produced by reacting the biocompatible functional group of the modified polylactide polymer described herein with a therapeutic agent, a diagnostic agent, a hydrophilic component, a hydrophobic component, or a combination thereof.

The modified polylactide polymer conjugate can be used to fabricate an implantable medical device, e.g., stent, or coating thereof described herein. The modified polylactide polymer conjugate can provide therapeutic effect, biobeneficial effect, or modify the surface property of the implantable medical device, depending on the component being conjugated to the modified polylactide polymer.

Conjugate with Therapeutic Agent

In certain embodiments, it is provided a modified polylactide polymer conjugate produced by reacting the biocompatible functional group of the modified polylactide polymer described herein with a therapeutic agent.

In certain embodiments, the therapeutic agent is selected from paclitaxel, rapamycin, rapamycn derivatives, everolimus, zotarolimus, temsirolimus, deforolimus, merilimus, novolimus, myolimus, umirolimus, biolimus, tacrolimus, pimecrolimus, 16-pent-2-ynyloxy-32(S)-dihydro-rapamycin, and ridaforolimus.

In certain embodiments, the therapeutic agent is an olimus drug. As used herein, and unless otherwise specified, the term "olimus drug" refers to a macrocyclic lactone chemical species which is a derivative, metabolite, or otherwise has a chemical structure similar to that of sirolimus and is useful for the treatment of neointimal hyperplasia and/or restenosis. Examples of "olimus drugs" include, but are not limited to, biolimus, merilimus, myolimus, novolimus, 16-pent-2-ynyloxy-32(S)-dihydro-rapamycin, ridaforolimus, tacrolimus, temsirolimus, and zotarolimus.

As used herein, unless otherwise specified, the terms "rapamycin" and "sirolimus" are used interchangeably, and refer to the compound having the following chemical structure:

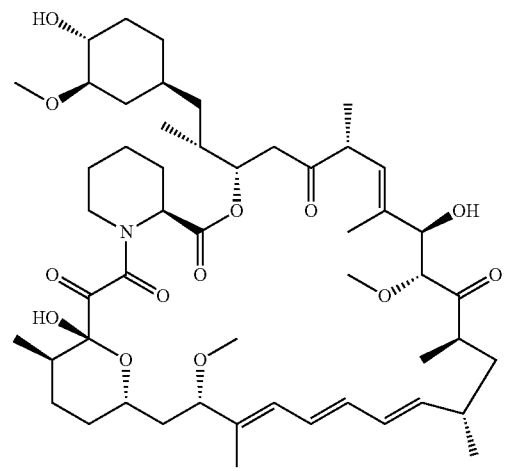 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

As used herein, and unless otherwise specified, the term "novolimus" refers to the compound having the following chemical structure:

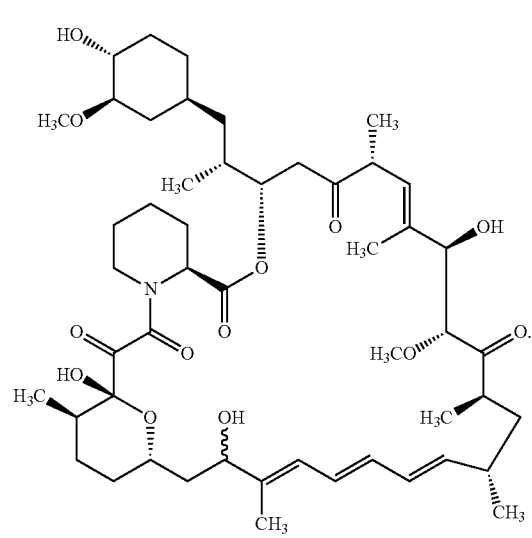 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(O)C[C@@H]3CC[C@@H](C)[C@@](O)(O3)C(=O)C(=O)N3CCCC[C@H]3C(=O)O2)CC[C@H]1O]

"Novolimus" is described in the following US Patent documents: U.S. Pat. No. 7,867,988 B2; U.S. Pat. No. 8,367,081 B2; and U.S. Pat. No. 8,404,641 B2.

In certain embodiments, the therapeutic agent is novolimus. Novolimus, via one of its four hydroxyl end groups can react with the carboxyl end group of a PLA polymer. Combination of the two, particularly with added acid catalyst and heat, will create an ester bond between the species, as shown in the scheme below:

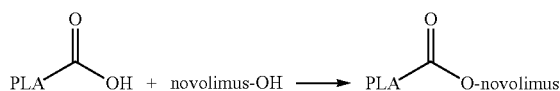

The above reaction can be carried out by one of the following procedures: dissolving novolimus and a PLA bearing carboxyl functional group(s) in chloroform; refluxing the solution at 61° C., the boiling point of chloroform; and collecting the distillate and running it through molecular sieves to remove all water and return to the reactor. Addition of an acid catalyst is not absolutely necessary; a small amount of HCl is optional.

Conjugate with a Diagnostic Agent

In certain embodiments, it is provided a modified polylactide polymer conjugate produced by reacting the biocompatible functional group of the modified polylactide polymer described herein with a diagnostic agent.

Exemplary diagnostic agents include, but are not limited to, radiocontrast agents. Exemplary radiocontrast agents include, but are not limited to:

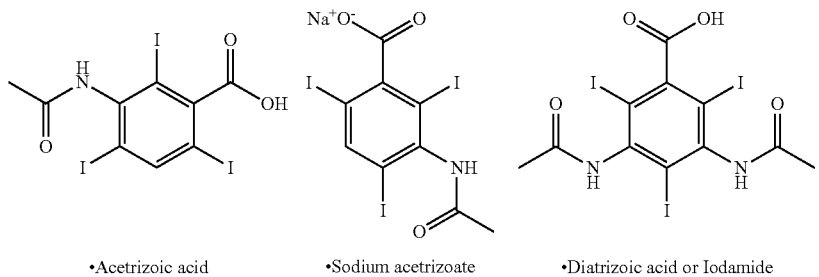

• Acetrizoic acid    • Sodium acetrizoate    • Diatrizoic acid or Iodamide

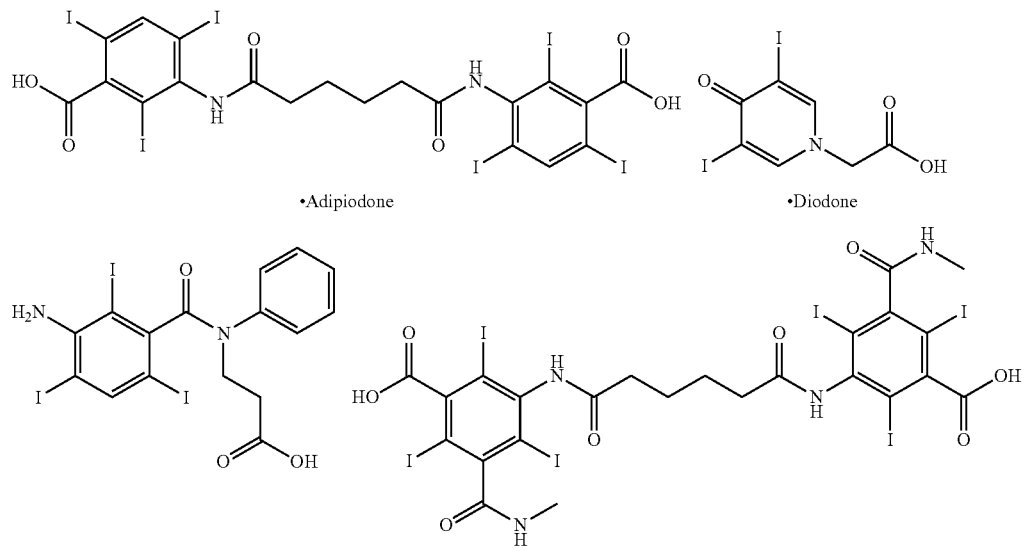

• Adipiodone    • Diodone

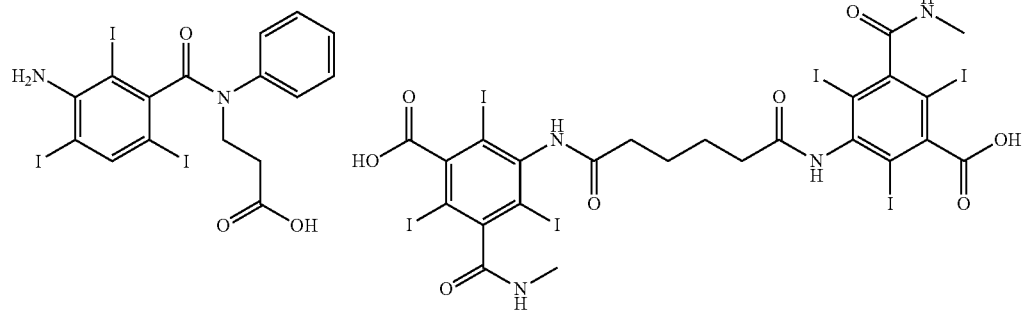

• Iobenzamic acid    • Iocarmic acid

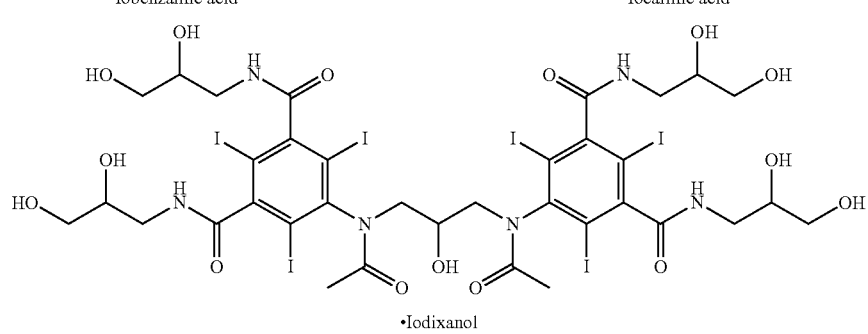

• Iodixanol

-continued
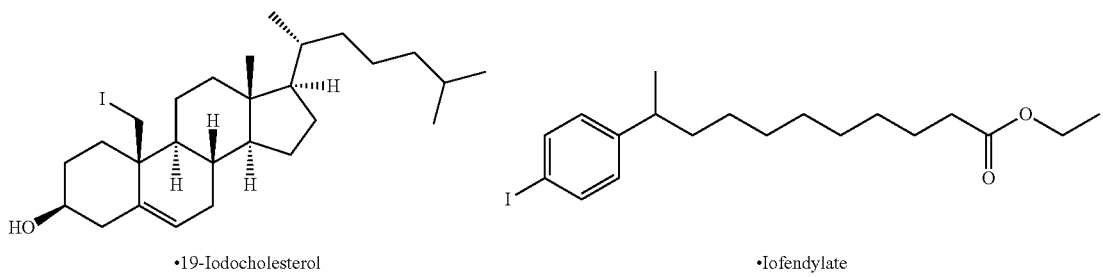
• 19-Iodocholesterol          • Iofendylate
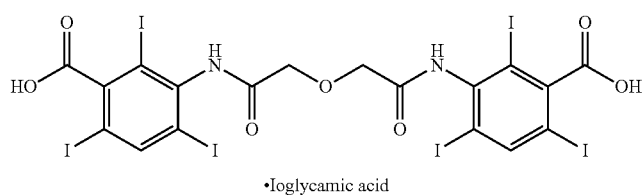
• Ioglycamic acid
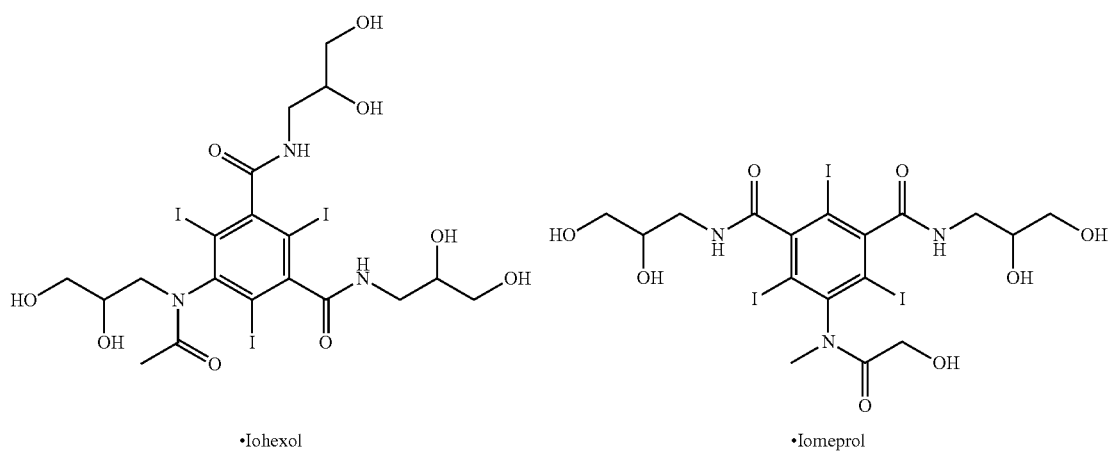
• Iohexol          • Iomeprol
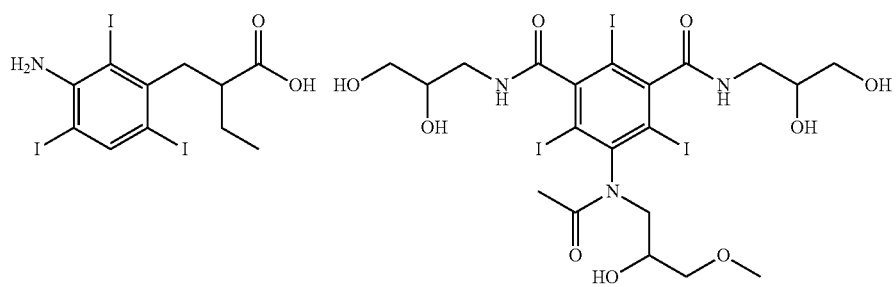
• Iopanoic acid          • Iopentol
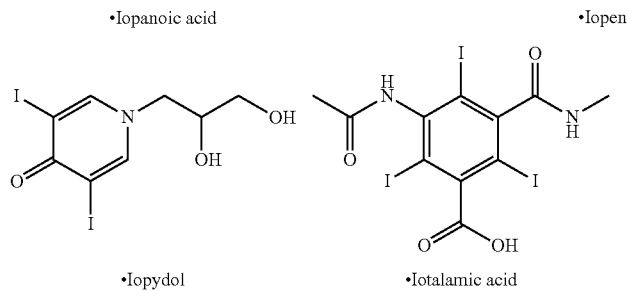
• Iopydol          • Iotalamic acid

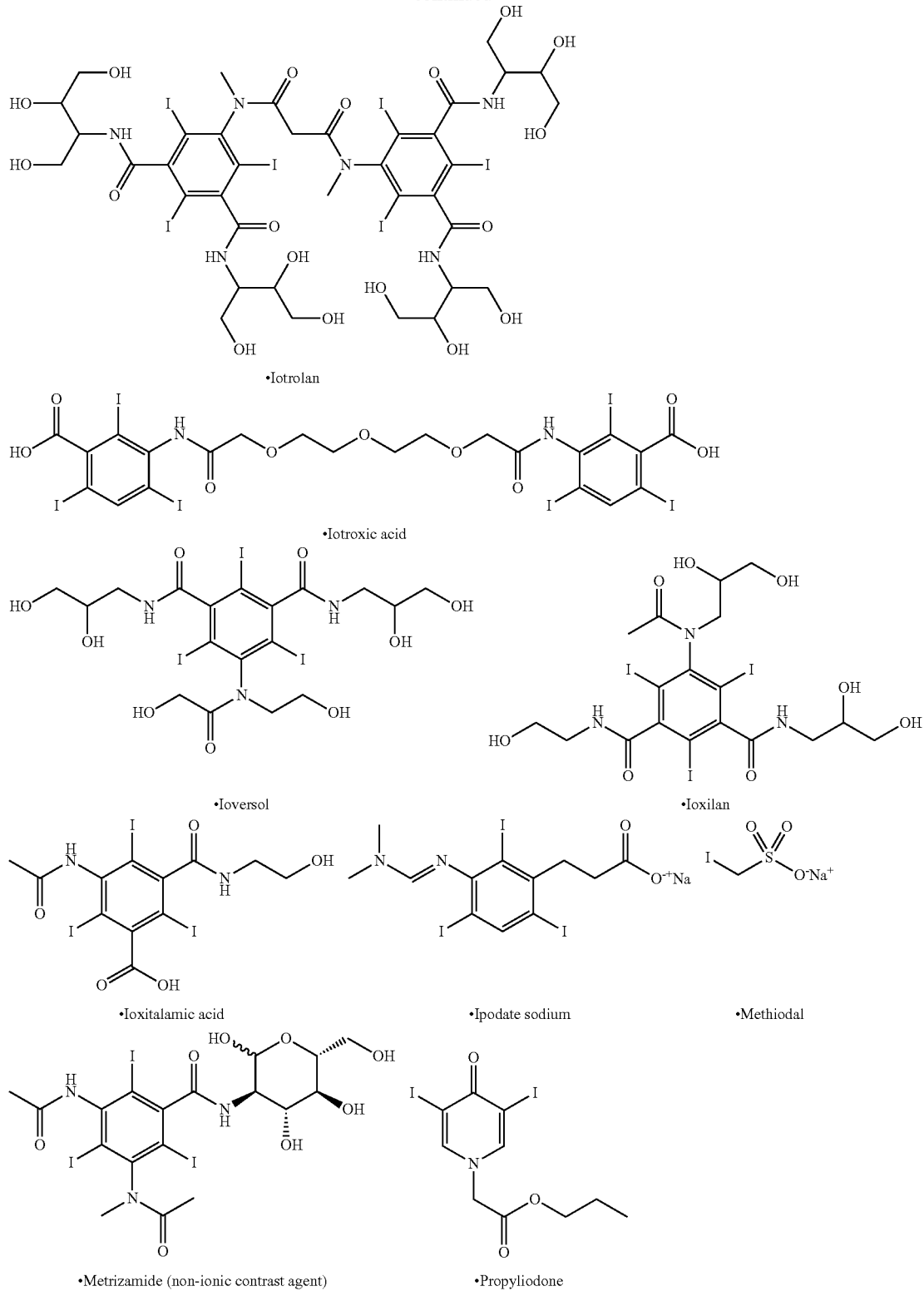

- Iotrolan
- Iotroxic acid
- Ioversol
- Ioxilan
- Ioxitalamic acid
- Ipodate sodium
- Methiodal
- Metrizamide (non-ionic contrast agent)
- Propyliodone Conjugate with a Hydrophilic Component In certain embodiments, it is provided a modified polylactide polymer conjugate produced by reacting the biocompatible functional group of the modified polylactide polymer described herein with a hydrophilic component.

Whether a material is hydrophobic or hydrophilic can be relative. One of the measurements of hydrophilicity/hydrophobicity is Hildebrand solubility parameter which a measure of the cohesive energy density, or polarity of a substance. Between different materials, whichever has a lower Hildebrand value (δ) value compared to the δ value of the other is designated as a hydrophobic, and the material with higher Hildebrand value (δ) value is designated as a hydrophilic.

In certain embodiments, the δ value defining the boundary between hydrophobic and hydrophilic can be about 11.5 $(cal/cm^3)^{1/2}$. Accordingly, hydrophobic is defined as having a δ value about 11.5 $(cal/cm^3)^{1/2}$ or lower, and hydrophilic is defined as having a δ value of about 11.5 $(cal/cm^3)^{1/2}$ or higher.

Exemplary hydrophilic components include but are not limited to poly(ethylene oxide) or poly(ethylene glycol) (PEG) and copolymer thereof such as poly(ethylene oxide-co-lactic acid) (PEO/PLA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol); PolyActive™ (block copolymer having flexible poly(ethylene glycol terephthalate) and poly(butylene terephthalate) blocks (PEGT/PBT)), including AB, ABA, BAB block copolymers having such segments of PEGT and PBT (e.g., poly(ethylene glycol terephthalate)-block-poly(butyleneterephthalate)-block-poly(ethylene glycol terephthalate) (PEGT-PBT-PEGT); polymers and copolymers of monomers bearing hydroxyl, carboxylic acid, phosphorylcholine, PEG, and/or other hydrophilic groups, such as hydroxylethyl methacrylate (HEMA), hydroxypropyl methacrylate (HPMA), hydroxypropyl methacrylamide, PEG acrylate (PEGA), PEG methacrylate, 2-methacryloyloxyethylphosphorylcholine (MPC), vinyl alcohol, allyl alcohol, n-vinyl pyrrolidone (VP), methacrylic acid (MA), acrylic acid (AA), alkoxymethacrylate, alkoxyacrylate, and 3-trimethylsilylpropyl methacrylate (TMSPMA); polybiomolecules such as collagen, chitosan, alginate, fibrin, fibrinogen, cellulose, starch, dextran, hyaluronic acid, fragments and derivatives of hyaluronic acid, heparin, fragments and derivatives of heparin, glycosamino glycan (GAG), GAG derivatives, polysaccharide, elastin, and combinations thereof.

In certain embodiments, the hydrophilic component can be conjugated to the PLA polymer using conventional chemistry such as esterification reaction between acid functional group on the PLA polymer and hydroxyl function group in the hydrophilic component, or vice versa.

Conjugate with a Hydrophobic Component

In certain embodiments, it is provided a modified polylactide polymer conjugate produced by reacting the biocompatible functional group of the modified polylactide polymer described herein with a hydrophobic component.

Exemplary useful hydrophobic components include but are not limited to saturated and unsaturated fatty acids and saturated and unsaturated fatty alcohols. Exemplary saturated and unsaturated fatty acids include but are not limited to castor oil, laureate, stearate, palmitate and oleate. Exemplary saturated and unsaturated fatty alcohols include but are not limited to hexanol, dodecanol, stanol, sterol, cholesterol, and cetyl.

In certain embodiments, the hydrophobic component is a hydrophobic polymer. Exemplary hydrophobic polymers include, but are not limited to, polycaprolactone, poly(ester amide), poly(ester amide) bearing hydrophobic pendant group(s), poly(tyrosine ester) and derivatives thereof, poly (imino carbonate), poly(phosphoester), polyphosphazene, polyamide, polyurethane, polyolefin or polyalkylene, poly (propylene oxide), poly(trimethylene oxide), alkylene vinyl acetate copolymers such as ethylene vinyl acetate (EVA), poly(ethyl methacrylate), poly(n-butyl methacrylate) (PBMA), polymer and copolymer of hydroxyalkanoates (HA).

Exemplary hydroxyalkanoate include but are not limited to 2-hydroxyalkanoates, 3-hydroxyalkanoates, or 4-hydroxyalknaote. 3-hydroxyalkanoates include but are not limited to 3-hydroxypropanoate, 3-hydroxybutyrate, 3-hydroxyvalerate, 3-hydroxyhexanoate, 3-hydroxyheptanoate and 3-hydroxyoctanoate. 4-hydroxyalknaotes include but are not limited to 4-hydroxybutyrate, 4-hydroxyvalerate, 4-hydroxyhexanote, 4-hydroxyheptanoate, and 4-hydroxyoctanoate.

In certain embodiments, the hydrophobic component can be conjugated to the PLA polymer using conventional chemistry such as esterification reaction between acid functional group on the PLA polymer and hydroxyl function group in the hydrophobic component, or vice versa.

Implantable Medical Device

It is provided herein an implantable medical device comprising a device body and optionally a coating partially or completely covering the surface of the device body. As used herein, a device body is also referred to as a device substrate and the terms "device body" and "device substrate" can be used interchangeably. The implantable medical device can be used for the treatment of restenosis, thrombosis, atherosclerosis, vulnerable plaque, and other vascular diseases. In certain embodiments, the implantable medical device is a stent. Stent body is also referred to as a "scaffold" in applications where the implant is designed to be temporary.

In certain embodiments, the implantable medical device is selected from stents, grafts, stent-grafts, catheters, leads and electrodes, clips, shunts, closure devices, and valves.

In certain embodiments, both the substrate and the coating comprise or are formed of the modified PLA polymer described herein. In certain embodiments, both the substrate and the coating comprise or are formed of the modified PLA polymer conjugate described herein.

In certain embodiments, only the substrate comprises or is formed of the modified PLA polymer described herein. In certain embodiments, only the substrate comprises or is formed of the modified PLA polymer conjugate described herein.

In certain embodiments, only the coating comprises or is formed of the modified PLA polymer described herein. In certain embodiments, only the coating comprises or is formed of the modified PLA polymer conjugate described herein.

In certain embodiments, the implantable medical device described herein is microparticles or nanoparticles comprising the modified PLA polymer(s) and/or the modified PLA polymer conjugate described herein.

In certain embodiments, both the substrate and the coating of the implantable medical device comprise microparticles or nanoparticles comprising the modified PLA polymer and/or the modified PLA polymer conjugate described herein.

In certain embodiments, only the substrate or only the coating of the implantable medical device comprises microparticles or nanoparticles comprising the modified PLA polymer and/or the modified PLA polymer conjugate described herein.

The substrate or the coating may comprise or be formed of one or more other bioabsorbable polymers. Suitable bioabsorbable polymers for forming a substrate or a coating include, but are not limited to, polylactide (PLA), polyglycolide (PGA), poly(D,L-lactide) (PDLLA), polycaprolactone (PCL), poly(trimethylene carbonate) (PTMC), poly(L- lactide-co-caprolactone) (PLLA-CL), poly(D-lactide-co-caprolactone) (PDLA-CL), poly(DL-lactide-co-caprolactone) (PDLLA-CL), poly(D-lactide-glycolide) (PDLA-GA), poly(L-lactide-glycolide) (PLLA-GA), poly(DL-lactide-glycolide) (PDLLA-GA), poly(L-lactide-co-caprolactone) (PLLA-CL), poly(D-lactide-co-caprolactone) (PDLA-CL), poly(DL-lactide-co-caprolactone) (PDLLA-CL), poly(glycolide-co-caprolactone) (PGA-CL), poly(L-lactide-co-trimethylene carbonate) (PLLA-TMC), poly(D-lactide-co-trimethylene carbonate) (PDLA-TMC), poly(D,L-lactide-co-trimethylene carbonate) (PDLLA-TMC), poly(glycolide-co-trimethylene carbonate) (PGA-TMC), poly(N-acetylglucosamine) (Chitin), Chitosan, polyhydroxyalkanoates, poly(hydroxyvalerate), poly(hydroxybutyrate), poly(hydroxybutyrate-co-valerate), poly(thioesters), poly(ether-co-esters) (e.g., PEO/PLA), polyphosphazenes, biomolecules (e.g., fibrin, fibrinogen, cellulose, starch, collagen and hyaluronic acid), polyamides (e.g., Nylon 66 and polycaprolactam), poly(N-vinyl pyrrolidone), polydioxanone, polyorthoesters, poly(tyrosine ester), polyanhydrides, polycarbonates, polyphosphoesters, polyphosphoester urethanes, poly(amino acids), poly(iminocarbonates), polyoxymethylenes, polyamides, poly(ester amides), polyimides, polyethers, polyurethanes, rayon, rayon-triacetate, cellulose and derivatives thereof (e.g., cellulose acetate, cellulose butyrate, cellulose acetate butyrate, cellophane, cellulose nitrate, cellulose propionate, cellulose ethers, and carboxymethyl cellulose), copolymers thereof, and blends thereof.

In certain embodiments, any of the aforementioned PLA-based copolymers have a constitutional unit weight-to-weight ratio of lactide and another monomer of about 1:99 to about 99:1, for example, about 5:95, about 10:90, about 20:80, about 30:70, about 40:60, about 50:50, about 60:40, about 70:30, about 80:20, about 90:10, about 95:5, about 93:7, about 94:6, about 95:5, about 96:4, about 97:3, about 98:2, or about 99:1. For example, the poly(lactide-co-caprolactone), poly(L-lactide-co-caprolactone), poly(D-lactide-co-caprolactone), and poly(D,L-lactide-co-caprolactone) have a constitutional unit weight-to-weight ratio of lactide and caprolactone of about 95/5, about 96/4, about 97/3, about 98/2, or about 99/1. For another example, the poly(lactide-co-caprolactone), poly(L-lactide-co-glycolide), poly(D-lactide-co-glycolide), and poly(D,L-lactide-co-glycolide) have a constitutional unit weight-to-weight ratio of lactide and glycolide of about about 60/40, about 65/35, about 70/30, about 75/25, about 80/20, about 85/15, about 90/10, or about 95/5.

In certain embodiments, the glass transition temperature ($T_g$) of the PLA-based polymer is selected over the range of 20° C. to 75° C. In one embodiment, the PLA-based polymer comprises poly(D,L-lactide) and the glass transition temperature ($T_g$) is selected over the range of 55° C. to 62° C.

In certain embodiments, the weight average molecular weight ($M_w$) of the aforementioned PLA-based polymer is selected over the range of 2,000 Daltons to 2,000,000 Daltons. In certain embodiments, a PLA-based polymer substrate comprises poly(L-lactide-co-caprolactone) or poly(D,L-lactide) and the weight average molecular weight ($M_w$) is selected over the range of 2,000 Daltons to 2,000,000 Daltons. In certain embodiments, a PLA-based polymer coating comprises poly(L-lactide-co-caprolactone) or poly(D,L-lactide) having a number average molecular weight ($M_n$) selected over the range of 10,000 Daltons to 1,000,000 Daltons.

The substrate and/or coating material can be a blend of two or more PLA-based polymers, or a PLA-based polymer with other biocompatible polymers described herein or known in the art.

In certain embodiments, the implantable medical device is a stent. In certain embodiments, the stent is a bioabsorbable stent. The bioabsorbable stent can be self-expandable stent or balloon-expandable stent.

Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. Stents are typically composed of a scaffold or scaffolding that includes a pattern or network of interconnecting structural elements or struts, formed from wires, tubes, or sheets of material rolled into a cylindrical shape. This scaffold or scaffolding gets its name because it physically holds open and, if desired, expands the wall of the passageway. Typically, stents are capable of being compressed or crimped onto a catheter so that they can be delivered to and deployed at a treatment site.

In certain embodiments, the crystallinity of the PLA-based polymer forming the stent scaffold is about 10% to about 70%, more narrowly about 40% to about 55%. In certain embodiments, the crystallinity is about 20% to about 30%, more narrowly about 27%.

The scaffold may have lengths of between 8 and 40 mm, and 18 and 36 mm, or even between 40 and 200 mm as fabricated or when implanted in a peripheral artery. Exemplary lengths include 8 mm, 12 mm, 14 mm, 18 mm, 28 mm, 33 mm, or 38 mm.

The stent may have a pre-crimping or as-fabricated diameter of between 2 and 3 mm, 2.5 and 3.5 mm, 3 and 4 mm, 3 and 5 mm, 5 and 10 mm, 6 and 8 mm, or any value between and including these endpoints. Diameter may refer to the inner diameter or outer diameter. Exemplary diameters include about 2.25 mm, about 2.5 mm, about 3.0 mm, about 3.25 mm, about 3.5 mm, about 4 mm, about 5 mm, or about 6 mm. The scaffold may have a radial wall thickness of about 100 microns, about 80 to 150 microns, 150 to 200 microns, 200 to 250 microns, 250 to 300 microns, 300 to 350 microns, 350 to 400 microns, or greater than 400 microns.

The scaffold may be configured for being deployed by a non-compliant or semi-compliant balloon from about 1.8 to about 2.2 mm diameter (e.g., 2 mm) crimped profile. Exemplary balloon sizes include about 2.5 mm, about 3 mm, about 4 mm, about 5.5 mm, about 5 mm, about 5.5 mm, about 6 mm, about 6.5 mm, about 7 mm, or about 8 mm, where the balloon size refers to a nominal inflated diameter of the balloon. The scaffold may be deployed to a diameter of between 2.5 mm and 3 mm, 3 mm and 3.5 mm, 3.5 mm and 4 mm, 4 mm and 10 mm, 7 and 9 mm, or any value between and including the endpoints.

In certain embodiments, the scaffold is in a crimped diameter over and in contact with a deflated catheter balloon.

In certain embodiments, the stent may be implanted in the cerebral, carotid, coronary, aortic, renal, iliac, femoral, popliteal, tibial, or other peripheral vasculature. The stent may be used in any artery, vein or vessel in the body in addition to coronary vessels.

Stents fabricated from bioabsorbable materials such as bioabsorbable polymers can be designed to completely absorb only after the clinical need for them has ended. Consequently, a fully bioabsorbable stent can reduce or eliminate the risk of potential long-term complications and of late thrombosis and facilitate non-invasive diagnostic MRI/CT imaging.

Implantable Medical Device for Drug Delivery

In accordance to an embodiment which can be used with any of the aforementioned embodiments above, it is provided herein an implantable medical device for delivering one or more therapeutic agents to the site of action or near the site of action.

In certain embodiments, optionally in combination with other embodiments, one or more therapeutic agents are embedded or impregnated in the substrate and/or the coating.

In some embodiments, a therapeutic agent is delivered to the site of action (e.g., a lumen of a blood vessel) from both the coating and substrate. In some embodiments, the therapeutic agent is delivered to the site of action in a two-stage process in which the therapeutic agent is released from the coating and the substrate at different rates.

In some embodiments, one or more therapeutic agents are embedded or impregnated only in the coating. The substrate may be free of therapeutic agent or a particular type of therapeutic agent other than incidental diffusion of agent into the scaffold from the polymer matrix.

In some embodiments, one or more therapeutic agents are embedded or impregnated only in the substrate. The coating may be free of therapeutic agent or a particular type of therapeutic agent other than incidental diffusion of agent into the substrate from the coating.

In some embodiments, the coating is absent and one or more therapeutic agents are embedded or impregnated in the substrate.

The therapeutic agent may be released from the implantable medical device by diffusion from the polymer, by hydrolysis of the polymer, or by erosion of the polymer. In certain embodiments, where the modified polylactide polymer conjugate with a therapeutic agent is used, the therapeutic agent can be released by first breaking the bond with the modified polylactide polymer.

The drug release rate may be controlled by adjusting the weight ratio of drug and coating material in the drug reservoir, the thickness of the coating, using a release control layer on top of the drug reservoir layer, and any combinations thereof.

The weight ratio of drug and coating material in the drug reservoir can range from 10:1 to 1:10. In certain embodiments, the weight ratio of drug and coating material in the drug reservoir is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10.

The coating can have a range of thickness over an implantable device. In certain embodiments, the coating has a thickness of ≤about 50 microns, ≤about 30 microns, ≤about 20 microns, ≤about 15 microns, ≤about 10 microns, or ≤about 5 microns. In one preferred embodiment, the coating is ≤about 3 microns thick.

The therapeutic agent may be released over a period of one to two weeks, up to one month, or up to three months to six months after implantation.

Method of Fabricating Implantable Medical Device

In certain embodiments, it is provided a method of fabricating an implantable medical device. In certain embodiments, the method is used to fabricate an implantable medical device selected from stents, grafts, stent-grafts, catheters, leads and electrodes, clips, shunts, closure devices, and valves.

In certain embodiments, the method comprises forming the implantable medical device substrate from a material containing the modified PLA polymer or the modified PLA polymer conjugate, and optionally one or more other materials that are suitable for forming an implantable medical device. A portion of the implantable medical device substrate or the whole substrate itself can be formed of the material.

In certain embodiments, the method is used to fabricate a stent. In certain embodiments, the method is used to fabricate a bioabsorbable stent. A method of fabricating a bioabsorbable stent can include the following steps:

(1) forming a polymeric tube from a bioabsorbable polymer resin using extrusion, (2) optionally radially deforming the formed tube to increase radial strength, (3) forming a stent scaffold from the tube or the deformed tube by laser machining a stent pattern in the tube or the deformed tube with laser cutting, and (4) optionally forming a coating over the stent scaffold.

The manufacturing process may further include the following steps:

(5) crimping the stent over a delivery balloon, and (6) sterilizing the stent.

In certain embodiments, a polymer or polymer conjugate described herein can be formed into a sheet that can be rolled or bonded to form a construct such as a tube. An implantable device can then be fabricated from the construct. For example, a stent can be fabricated from a tube by laser machining a pattern into the tube. In certain embodiments, a polymer construct can be formed using an injection-molding apparatus.

Examples of polymers that can be used to fabricate an implantable device substrate include, but are not limited to, polylactide (PLA), polyglycolide (PGA), poly(D,L-lactide) (PDLLA), polycaprolactone (PCL), poly(trimethylene carbonate) (PTMC), poly(L-lactide-co-caprolactone) (PLLA-CL), poly(D-lactide-co-caprolactone) (PDLA-CL), poly(DL-lactide-co-caprolactone) (PDLLA-CL), poly(D-lactide-glycolide) (PDLA-GA), poly(L-lactide-glycolide) (PLLA-GA), poly(DL-lactide-glycolide) (PDLLA-GA), poly(L-lactide-co-caprolactone) (PLLA-CL), poly(D-lactide-co-caprolactone) (PDLA-CL), poly(DL-lactide-co-caprolactone) (PDLLA-CL), poly(glycolide-co-caprolactone) (PGA-CL), poly(L-lactide-co-trimethylene carbonate) (PLLA-TMC), poly(D-lactide-co-trimethylene carbonate) (PDLA-TMC), poly(D,L-lactide-co-trimethylene carbonate) (PDLLA-TMC), poly(glycolide-co-trimethylene carbonate) (PGA-TMC), poly(N-acetylglucosamine) (Chitin), Chitosan, polyhydroxyalkanoates, poly(hydroxyvalerate), poly(hydroxybutyrate), poly(hydroxybutyrate-co-valerate), poly(thioesters), poly(ether-co-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides, polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), poly(N-vinyl pyrrolidone), polydioxanone, polyorthoesters, poly(tyrosine ester), polyanhydrides, polycarbonates, polyphosphoesters, polyphosphoester urethanes, poly(amino acids), poly(iminocarbonates), polyoxymethylenes, polyamides, poly(ester amides), polyimides, polyethers, polyurethanes, rayon, rayon-triacetate, cellulose and derivatives thereof (e.g., cellulose acetate, cellulose butyrate, cellulose acetate butyrate, cellophane, cellulose nitrate, cellulose propionate, cellulose ethers, and carboxymethyl cellulose), copolymers thereof, and blends thereof.

In certain embodiments, the coating is absent and the device substrate comprises or is formed of the modified PLA polymer or the modified PLA polymer conjugate described herein, optionally with one or more other materials suitable for forming a device substrate, such as those polymers described above.

In certain embodiments, a coating is disposed over the implantable device substrate. Suitable coating techniques include, but are not limited to, roller coating, ink jet printing, dip coating, and spray coating.

The coating can have a variety of constructs. In certain embodiments, the coating has one layer. The layer comprises a drug, a polymer, or both. In certain embodiments, the coating has a multi-layer structure that includes one or a combination of:

(1) a primer layer;
(2) a drug reservoir layer (also referred to "drug matrix"), which can be a drug-polymer layer including at least one polymer (drug-polymer layer) or, alternatively, a polymer-free drug layer;
(3) a release control layer (also referred to as a "rate-limiting layer");
(4) a topcoat layer; and/or
(5) a finishing coat layer which is present to modulate the biological response the coating.

In certain embodiments, the coating includes two or more reservoir layers described above; each can include a bioactive agent described herein.

Each layer of the coating can be disposed over the implantable medical device substrate (e.g., a stent) by dissolving the modified PLA polymer or the modified PLA polymer conjugate, described herein, optionally with one or more other material suitable for forming a coating, in a solvent, or a mixture of solvents, and disposing the resulting coating solution over the substrate by spraying or immersing the stent in the solution. After the solution has been disposed over the substrate, the coating is dried by allowing the solvent to evaporate. The process of drying can be accelerated if the drying is conducted at an elevated temperature.

To incorporate a drug into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by rolling, ink jet printing, direct fluid application, spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied indirectly over at least a portion of the stent surface to serve as a reservoir for at least one drug that is incorporated into the reservoir layer over at least a portion of the primer layer.

The optional primer layer can be applied between the stent and the reservoir to improve the adhesion of the drug-polymer layer to the stent.

The optional topcoat layer can be applied over at least a portion of the reservoir layer and serves as a rate-limiting membrane that helps to control the rate of release of the drug. In certain embodiments, the topcoat layer is essentially free from any bioactive agents or drugs.

If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Any layer of the coating can contain any amount of a bioabsorbable polymer. Examples of such polymers include but are not limited to bioabsorbable polymers and biocompatible polymers including, but not limited to, polylactide (PLA), polyglycolide (PGA), poly(D,L-lactide) (PDLLA), polycaprolactone (PCL), poly(trimethylene carbonate) (PTMC), poly(L-lactide-co-caprolactone) (PLLA-CL), poly(D-lactide-co-caprolactone) (PDLA-CL), poly(DL-lactide-co-caprolactone) (PDLLA-CL), poly(D-lactide-glycolide) (PDLA-GA), poly(L-lactide-glycolide) (PLLA-GA), poly(DL-lactide-glycolide) (PDLLA-GA), poly(L-lactide-co-caprolactone) (PLLA-CL), poly(D-lactide-co-caprolactone) (PDLA-CL), poly(DL-lactide-co-caprolactone) (PDLLA-CL), poly(glycolide-co-caprolactone) (PGA-CL), poly(L-lactide-co-trimethylene carbonate) (PLLA-TMC), poly(D-lactide-co-trimethylene carbonate) (PDLA-TMC), poly(D,L-lactide-co-trimethylene carbonate) (PDLLA-TMC), poly(glycolide-co-trimethylene carbonate) (PGA-TMC), poly(N-acetylglucosamine) (Chitin), Chitosan, polyhydroxyalkanoates, poly(hydroxyvalerate), poly(hydroxybutyrate), poly(hydroxybutyrate-co-valerate), poly(thioesters), poly(ether-co-esters) (e.g., PEO/PLA), polyphosphazenes, biomolecules (e.g., fibrin, fibrinogen, cellulose, starch, collagen and hyaluronic acid), polyamides (e.g., Nylon 66 and polycaprolactam), poly(N-vinyl pyrrolidone), polydioxanone, polyorthoesters, poly(tyrosine ester), polyanhydrides, polycarbonates, polyphosphoesters, polyphosphoester urethanes, poly(amino acids), poly(iminocarbonates), polyoxymethylenes, polyamides, poly(ester amides), polyimides, polyethers, polyurethanes, rayon, rayon-triacetate, cellulose and derivatives thereof (e.g., cellulose acetate, cellulose butyrate, cellulose acetate butyrate, cellophane, cellulose nitrate, cellulose propionate, cellulose ethers, and carboxymethyl cellulose), copolymers thereof, and blends thereof.

Any layer of the coating can contain any amount of the modified PLA polymer or the modified PLA polymer conjugate described herein, for example, about 5%, 10%, 15%, 20%, 25%, 30%, 35%, 40%, 45%, 50%, 55%, 60%, 65%, 70%, 75%, 80%, 85%, 90%, 95%, or 100%. In certain embodiments, the drug reservoir layer comprises any amount of the modified PLA polymer or the modified PLA polymer conjugate described herein, in addition to any drug(s) or therapeutic agent(s). In certain embodiments, the primer layer or the topcoat comprises any amount of the modified PLA polymer or the modified PLA polymer conjugate described herein.

Sterilization of a coated medical device generally involves a process for inactivation of micropathogens. Such processes are well known in the art. Exemplary sterilization processes include, but are not limited to, E-beam, ethylene oxide sterilization (ETO sterilization), and gamma irradiation.

Method of Treating or Preventing Disorders

It is provided herein a method of treating, preventing, or diagnosing a condition or disorder using the implantable medical device provided herein. The method comprises implanting an implantable medical device provided herein in a subject in need of the treatment, prevention, or diagnosis.

In certain embodiments, optionally in combination with one or more other embodiments described herein, the method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis, or vulnerable plaque.

In one embodiment of the method, optionally in combination with one or more other embodiments described herein, the implantable medical device's substrate and/or coating contain at least one bioactive or therapeutic agent in a therapeutic effective amount.

Suitable therapeutic agents include, but are not limited to, anti-proliferative agents, anti-inflammatory agents, antineoplastics and/or anti-mitotics, antiplatelet agents, anticoagulant agents, anti-fibrin agents, and anti-thrombin agents, cytostatic or anti-proliferative agents, antibiotics, anti-allergic agents, antioxidants and other bioactive agents known to those skilled in the art.

Suitable anti-proliferative agents include, but are not limited to, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, tacrolimus, myolimus, merilimus, pimecrolimus, temsirolimus, deforolimus, ridaforolimus, rapamycin, rapamycin derivatives, novolimus, zotarolimus, FKBP-12 mediated mTOR inhibitors, biolimus, umirolimus, perfenidone, 40-O-(2-hydroxyethyl) rapamycin (EVEROLIMUS®), 40-O-(3-hydroxypropyl)rapamycin, 40-O-[2-(2-hydroxyl)ethoxy]ethyl-rapamycin, 40-O-tetrazolylrapamycin, 40-epi-(N1-tetrazolyl)-rapamycin, 16-pent-2-ynyloxy-32(S)-dihydro rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, codrugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

In certain embodiments, the amount of the therapeutic agent is about 3 to 7 micrograms per millimeter length of the implantable medical device.

In certain embodiments, it is provided herein a bioabsorbable implantable medical device comprising a device body and optionally a coating partially or completely covering the surface of the device body. In certain embodiments, either or both of the substrate and the coating comprise or are formed of the modified PLA polymer or the modified PLA polymer conjugate described herein, and either or both of the substrate and the coating comprises novolimus. In certain embodiments, the substrate comprises or is formed of the modified poly(L-lactide-co-caprolactone) described herein and further comprises novolimus. In certain embodiments, the coating comprises or is formed of the modified poly(L-lactide-co-caprolactone) described herein and further comprises novolimus. In certain embodiments, the implantable medical device is a bioabsorbable stent. In certain embodiments, novolimus is included in the scaffold of a bioabsorbable stent described herein. In certain embodiments, novolimus is included in the scaffold of a bioabsorbable stent described herein in the amount of about 5 micrograms per millimeter length of the stent. In certain embodiments, novolimus is included in the coating of a bioabsorbable stent described herein. In certain embodiments, novolimus is included in the coating of a bioabsorbable stent described herein in the amount of about 5 micrograms per millimeter length of the stent.

EXAMPLES

Example 1

E-Beam Treatment of PLLA Resins

PLLA resins were packed with argon and treated with e-beam at 31 kGy. Six new biocompatible functional groups (A-F) were produced, most of which are end groups. Among the new functional groups, A-C, E, and F are end groups, and D is in the backbone of the polymer.

The following new functional groups were determined by $^1$H-NMR technique. See Table 1. The concentration of the functional group is summarized in FIG. 1.

FIG. 1 shows quantification of peaks from device using Evonik Resins with 31 kGy e-beam, device using Purac PLLA Resins with 31 kGy e-beam, and device using Evonik PLLA Resins with 25 kGy e-beam (left to right).

TABLE 1

$^1$H-NMR Structure Assignment of the Chemical Groups

| 1H-NMR Peak (ppm) | Group ID | Structure (By 1H-NMR) |
|---|---|---|
| a: 517<br>b: 1.58<br>c: 4.36<br>d: 1.62<br>e: 2.67<br>f: 0.88<br>g: 1.26<br>g': 4.13<br>g": 1.50 | Resin Structure | |
| | Lauryl Alcohol end group (EG1) | |
| 8.08 | A | |
| CH2: 4.19<br>CH3: 1.27 | B | |
| CH2: 2.41<br>CH3: 1.16 | C | |

TABLE 1-continued

<sup>1</sup>H-NMR Structure Assignment of the Chemical Groups

| 1H-NMR Peak (ppm) | Group ID | Structure (By 1H-NMR) |
|---|---|---|
| 6.21<br>5.62 | D | —(O—C(=O)—CH(CH₃)—O)ₙ—C(=O)—CH₂—O—C(=O)—CH(CH₃)—O)ₙ— |
| CH2: 6.48 & 5.9<br>CH: 6.19 | E | —(—CH(CH₃)—O)ₙ—C(=O)—C(H)=CH₂ |
| 2.5 | F | —(—CH(CH₃)—O)ₙ—C(=O)—C(=O)—CH₃ |

Example 2

E-Beam Irradiation of PLLA Expanded Tubing

PLLA expanded tubing was divided into four study arms.
Arm 1—tubing was packed with nitrogen (Normal),
Arm 2—tubing was packed with nitrogen containing 1% $H_2$,
Arm 3—tubing was packed with nitrogen containing 4.3% IPA,
Arm 4—tubing was packed with nitrogen containing 21% $O_2$.

All four arms were treated with e-beam at 25 kGy. The same function groups listed in Table 1 were identified. However, the concentration of each functional group varies initially and changes over time for some study arms. The results are shown in FIGS. 2-7.

Figure 2:
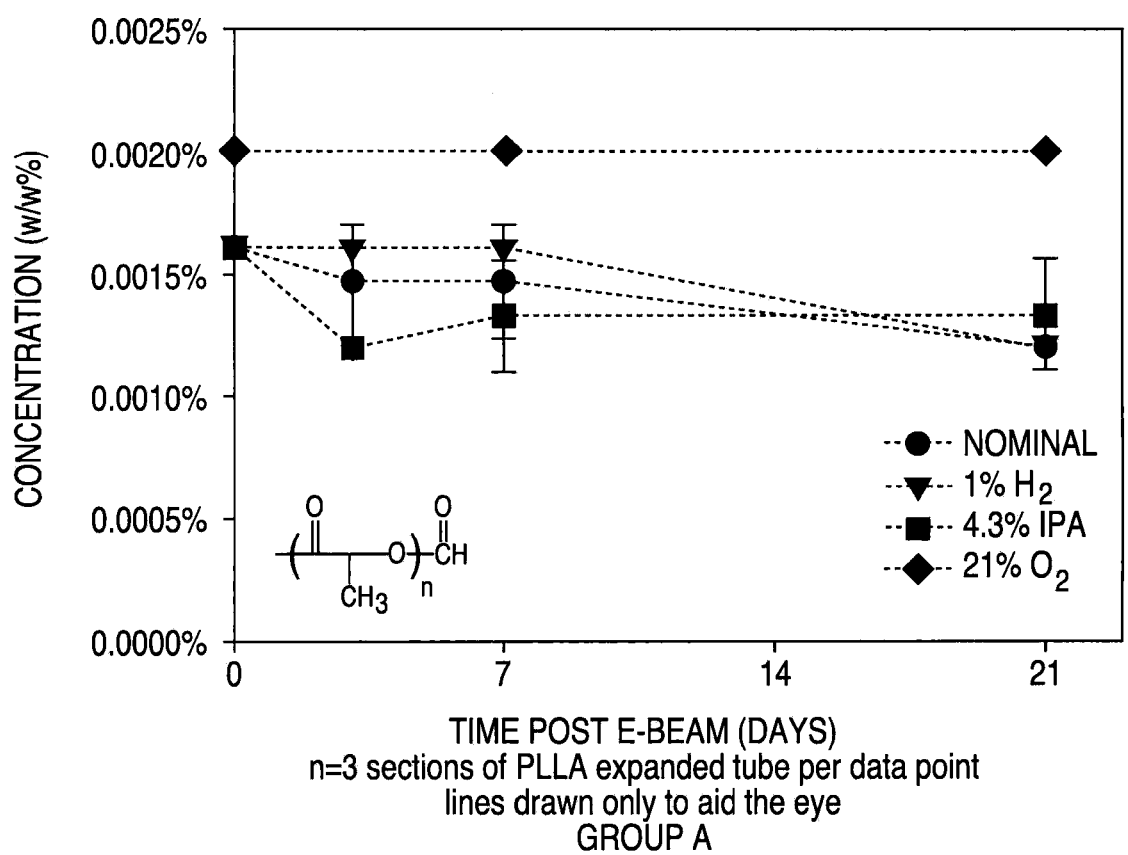
FIG. 2 shows the concentrations of the functional group A resulted from the four different treatments, Normal (Nitrogen), 1% $H_2$, 4.3% IPA, and 21% $O_2$.

FIG. 2 shows the concentrations of the functional group A resulted from the four different treatments, Normal (Nitrogen), 1% $H_2$, 4.3% IPA, and 21% $O_2$.

Figure 3:
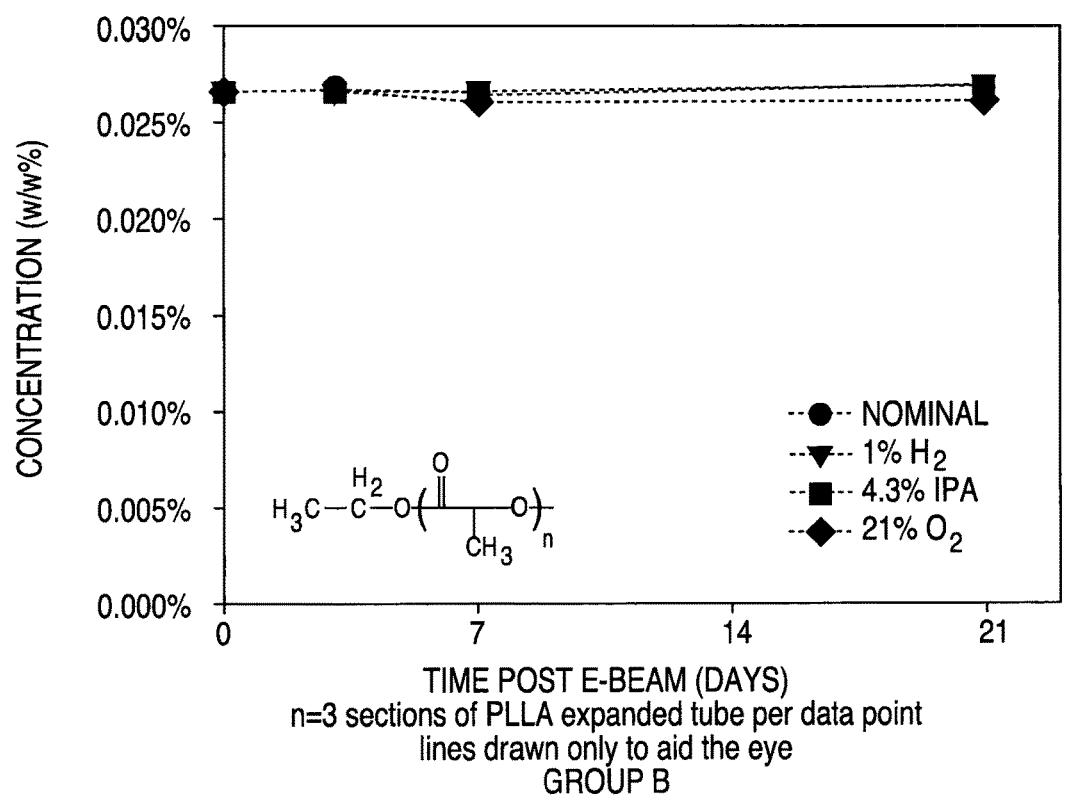
FIG. 3 shows the concentrations of the functional group B resulted from the four different treatments, Normal (Nitrogen), 1% $H_2$, 4.3% IPA, and 21% $O_2$.

FIG. 3 shows the concentrations of the functional group B resulted from the four different treatments, Normal (Nitrogen), 1% $H_2$, 4.3% IPA, and 21% $O_2$.

Figure 4:
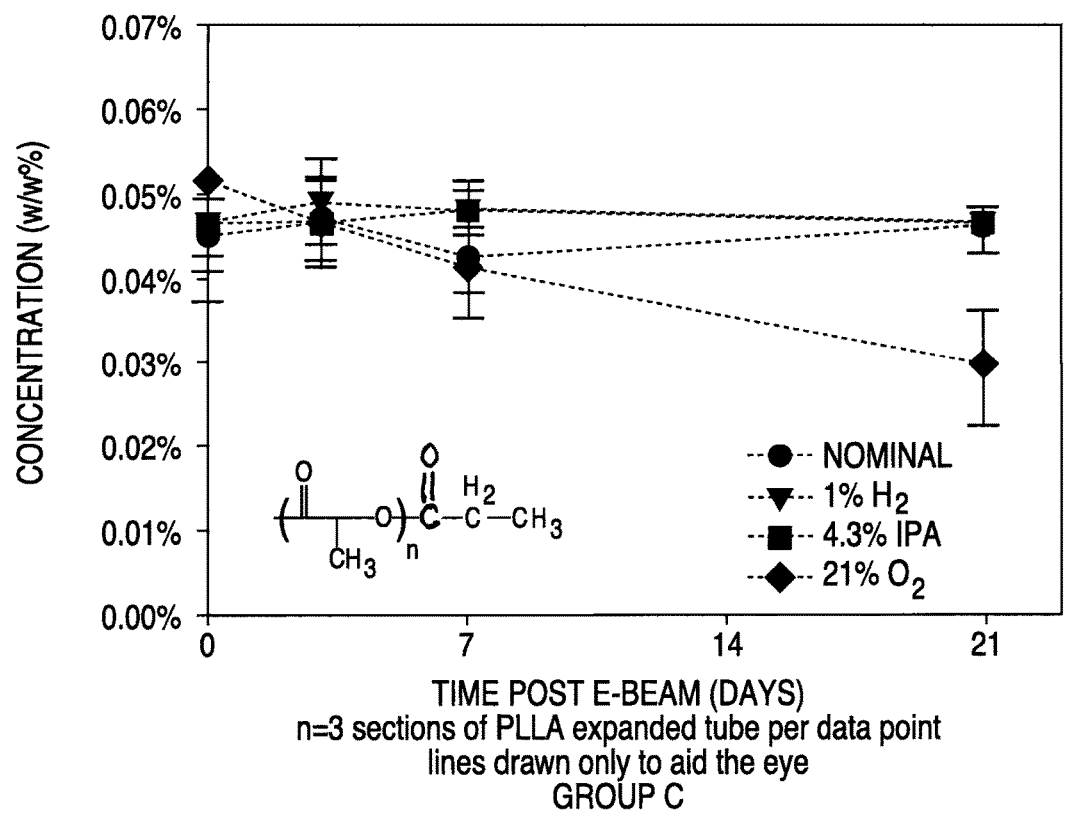
FIG. 4 shows the concentrations of the functional group C resulted from the four different treatments, Normal (Nitrogen), 1% $H_2$, 4.3% IPA, and 21% $O_2$.

FIG. 4 shows the concentrations of the functional group C resulted from the four different treatments, Normal (Nitrogen), 1% $H_2$, 4.3% IPA, and 21% $O_2$.

Figure 5:
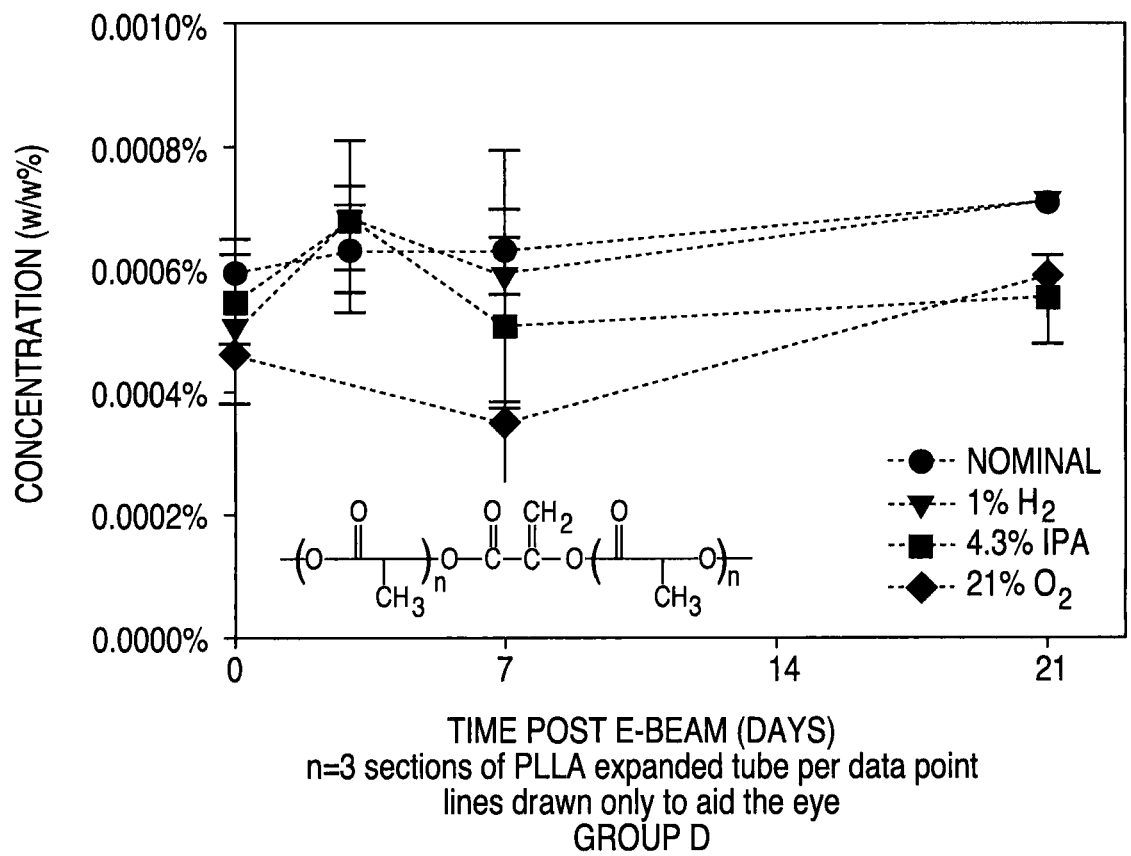
FIG. 5 shows the concentrations of the functional group D resulted from the four different treatments, Normal (Nitrogen), 1% $H_2$, 4.3% IPA, and 21% $O_2$.

FIG. 5 shows the concentrations of the functional group D resulted from the four different treatments, Normal (Nitrogen), 1% $H_2$, 4.3% IPA, and 21% $O_2$.

Figure 6:
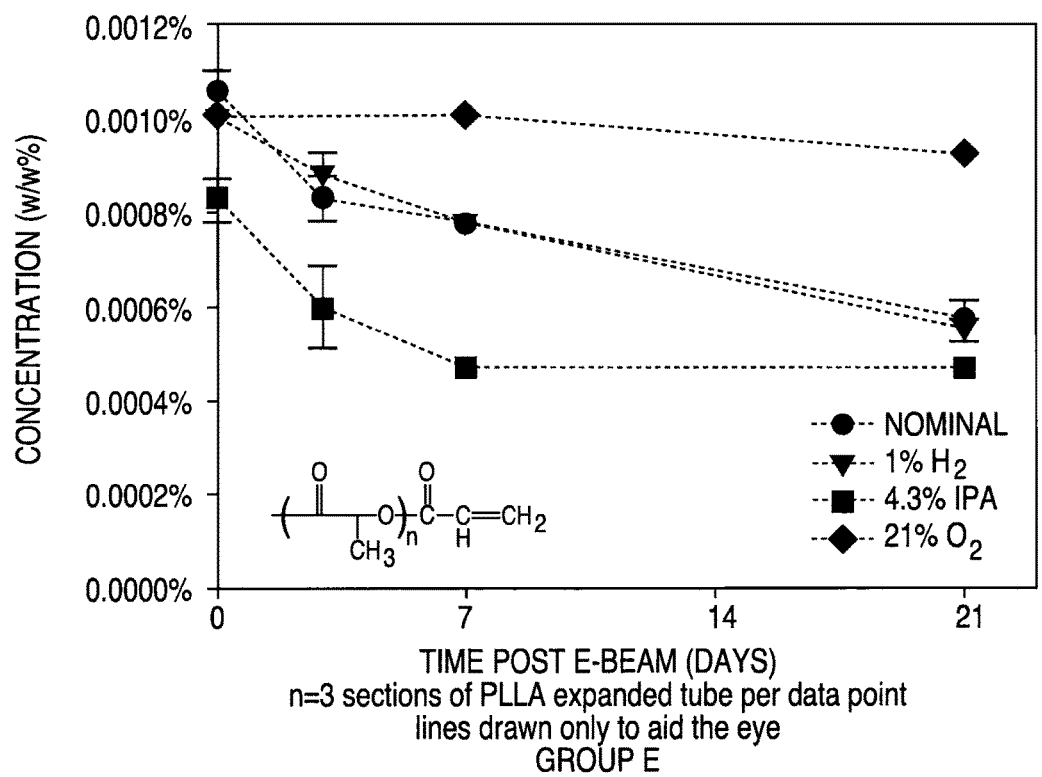
FIG. 6 shows the concentrations of the functional group E resulted from the four different treatments, Normal (Nitrogen), 1% $H_2$, 4.3% IPA, and 21% $O_2$.

FIG. 6 shows the concentrations of the functional group E resulted from the four different treatments, Normal (Nitrogen), 1% $H_2$, 4.3% IPA, and 21% $O_2$.

Figure 7:
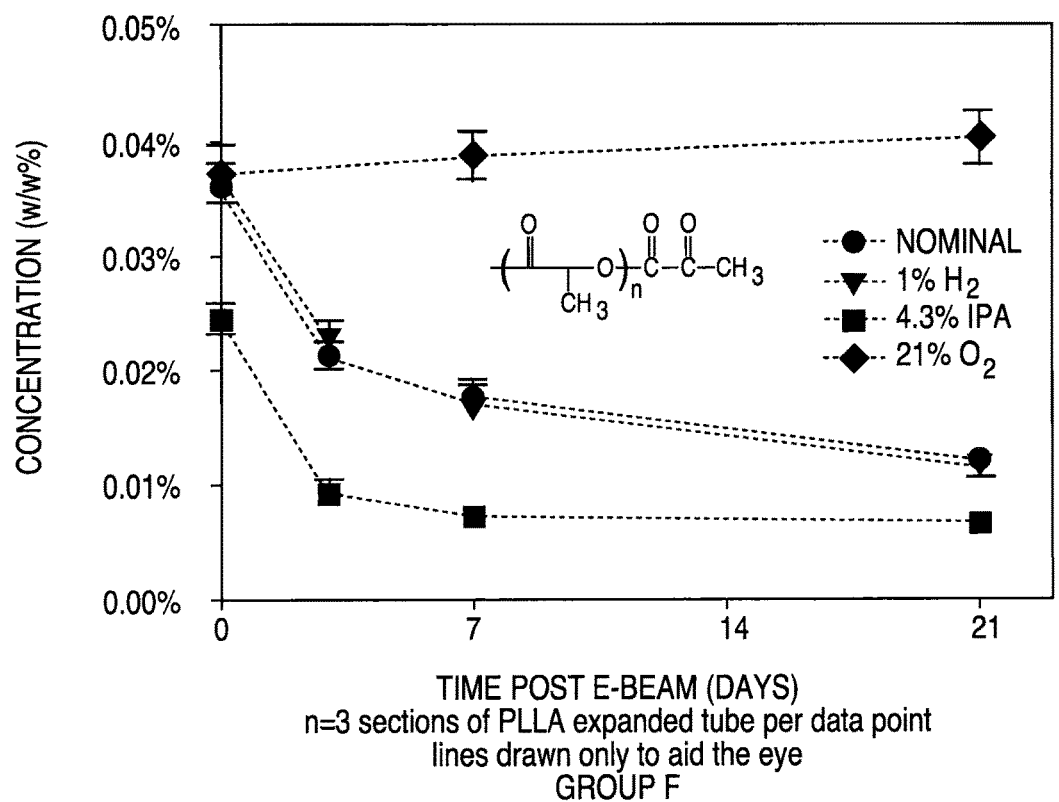
FIG. 7 shows the concentrations of the functional group F resulted from the four different treatments, Normal (Nitrogen), 1% $H_2$, 4.3% IPA, and 21% $O_2$.

FIG. 7 shows the concentrations of the functional group F resulted from the four different treatments, Normal (Nitrogen), 1% $H_2$, 4.3% IPA, and 21% $O_2$.

Example 3

Radiation Sterilization of PDLLA-GA and PLLA-GA

Poly(D,L-lactide-co-glycolide) (PDLLA-GA) and poly (L-lactide-co-glycolide) (PLLA-GA) are radiation sterilized. End groups formed include the following:

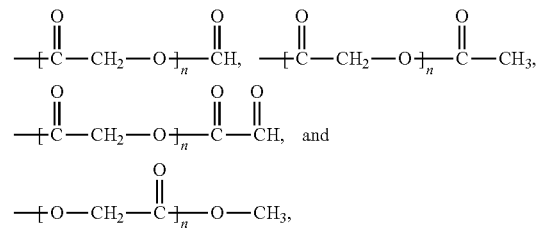

wherein n is a positive integer.

Example 4

Radiation Sterilization of PLA Copolymer Containing ε-Caprolactone

PLA copolymers containing ε-caprolactone are radiation sterilized and exposed to oxygen. End groups and group in the polymer backbone formed include the following:

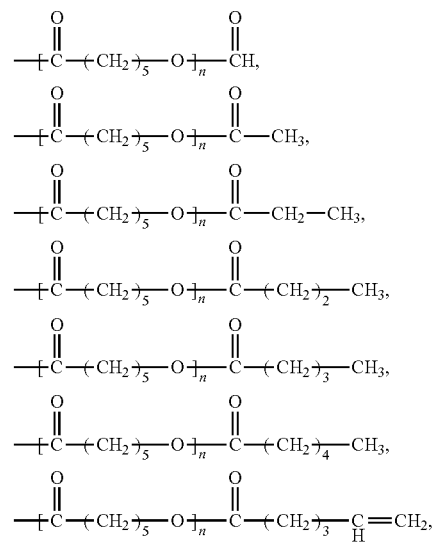

-continued $$-\!\!\left[\!\!\overset{O}{\underset{\|}{C}}\!\!-\!\!(CH_2)_5\!\!-\!\!O\right]_{\!\!n}\!\!\overset{O}{\underset{\|}{C}}\!\!-\!\!(CH_2)_4\!\!-\!\!\overset{O}{\underset{\|}{C}}\!\!H,$$

$$-\!\!\left[\!\!O\!\!-\!\!(CH_2)_5\!\!-\!\!\overset{O}{\underset{\|}{C}}\right]_{\!\!n}\!\!O\!\!-\!\!CH_3,$$

$$-\!\!\left[\!\!O\!\!-\!\!(CH_2)_5\!\!-\!\!\overset{O}{\underset{\|}{C}}\right]_{\!\!n}\!\!O\!\!-\!\!CH_2\!\!-\!\!CH_3,$$

$$-\!\!\left[\!\!O\!\!-\!\!(CH_2)_5\!\!-\!\!\overset{O}{\underset{\|}{C}}\right]_{\!\!n}\!\!O\!\!-\!\!(CH_2)_2\!\!-\!\!CH_3,$$

$$-\!\!\left[\!\!O\!\!-\!\!(CH_2)_5\!\!-\!\!\overset{O}{\underset{\|}{C}}\right]_{\!\!n}\!\!O\!\!-\!\!(CH_2)_3\!\!-\!\!CH_3,$$

$$-\!\!\left[\!\!O\!\!-\!\!(CH_2)_5\!\!-\!\!\overset{O}{\underset{\|}{C}}\right]_{\!\!n}\!\!O\!\!-\!\!(CH_2)_4\!\!-\!\!CH_3,$$

$$PCL\!\!-\!\!\overset{O}{\underset{\|}{C}}\!\!-\!\!(CH_2)_3\!\!-\!\!CH\!\!=\!\!CH_2\!\!-\!\!O\!\!-\!\!PCL,$$

$$PCL\!\!-\!\!\overset{O}{\underset{\|}{C}}\!\!-\!\!(CH_2)_2\!\!-\!\!CH\!\!=\!\!CH\!\!-\!\!CH_2\!\!-\!\!O\!\!-\!\!PCL,$$

$$PCL\!\!-\!\!\overset{O}{\underset{\|}{C}}\!\!-\!\!CH_2\!\!-\!\!CH\!\!=\!\!CH\!\!-\!\!(CH_2)_2\!\!-\!\!O\!\!-\!\!PCL, \text{ and}$$

$$PCL\!\!-\!\!\overset{O}{\underset{\|}{C}}\!\!-\!\!CH\!\!=\!\!CH\!\!-\!\!(CH_2)_3\!\!-\!\!O\!\!-\!\!PCL,$$

wherein m and n are independently a positive integer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A modified polylactide (PLA) polymer comprising a biocompatible functional group (BFG) on a PLA polymer, wherein the BFG is at one or both ends of the polymer backbone or in the polymer backbone;

wherein the modified polylactide polymer is according to one of the following formulae:

polylactide polymer-BFG3-polylactide polymer,

BFG1-polylactide polymer-BFG3-polylactide polymer-BFG2,

BFG1-polylactide polymer-BFG3-polylactide polymer, polylactide polymer-BFG3-polylactide polymer-BFG2;

wherein

BFG1 and BFG2 are independently selected from the group consisting of —H, —CH$_3$, —CH$_2$CH$_3$, —CH=CH$_2$, —CH=CH$_2$CH$_3$, $$\overset{O}{\underset{\|}{\sim\!\!\sim\!\!\sim\! C}}\!\!-\!\!H, \quad \overset{O}{\underset{\|}{\sim\!\!\sim\!\!\sim\! C}}\!\!-\!\!(CH_2)_y\!\!-\!\!CH_3, \quad \overset{O}{\underset{\|}{\sim\!\!\sim\!\!\sim\! C}}\!\!-\!\!(CH_2)_y\!\!-\!\!\overset{O}{\underset{\|}{C}}\!\!H,$$

$$\overset{O}{\underset{\|}{\sim\!\!\sim\!\!\sim\! C}}\!\!-\!\!(CH_2)_y\!\!-\!\!\overset{O}{\underset{\|}{C}}\!\!-\!\!CH_3, \quad \overset{O}{\underset{\|}{\sim\!\!\sim\!\!\sim\! C}}\!\!-\!\!(CH_2)_y\!\!-\!\!CH\!\!=\!\!CH_2,$$

$$\sim\!\!\sim\!\!\sim\! O\!\!-\!\!(CH_2)_z\!\!-\!\!CH_3, \text{ and } \sim\!\!\sim\!\!\sim\! O\!\!-\!\!(CH_2)_z\!\!-\!\!CH\!\!=\!\!CH_2;$$

wherein y is an integer ranging from 0 to 4 inclusive, and z is an integer ranging from 0 to 15 inclusive;

BFG3 is selected from the group consisting of $$\overset{O}{\underset{\|}{\sim\!\!\sim\!\!\sim\! C}}\!\!-\!\!(CH_2)_p\!\!-\!\!CH\!\!=\!\!CH\!\!-\!\!(CH_2)_q\!\!-\!\!O\!\!\sim\!\!\sim\!\!\sim \text{ and}$$

$$\overset{O}{\underset{\|}{\sim\!\!\sim\!\!\sim\! C}}\!\!-\!\!\overset{CH_2}{\underset{\|}{C}}\!\!-\!\!O\!\!\sim\!\!\sim\!\!\sim;$$

wherein p is an integer ranging from 0 to 3 inclusive, q is an integer ranging from 3 to 0 inclusive, provided p+q=3; and wherein the molecular weight of the polylactide polymer is from about 2,000 Daltons to about 2,000,000 Daltons.

2. The modified polylactide polymer of claim 1, wherein the PLA polymer is a homopolymer of lactide or a copolymer of lactide and at least one monomer.

3. The modified polylactide polymer of claim 2, wherein the at least one monomer is a hydroxy alkanoate monomer selected from the group consisting of glycolic acid, 3-hydroxypropanoate, 3-hydroxybutyrate, 3-hydroxyvalerate, 3-hydroxyhexanoate, 3-hydroxyheptanoate, 3-hydroxyoctanoate, 4-hydroxybutyrate, 4-hydroxyvalerate, 4-hydroxyhexanote, 4-hydroxyheptanoate, and 4-hydroxyoctanoate.

4. The modified polylactide polymer of claim 1, wherein the PLA polymer is selected from the group consisting of poly(L-lactide), poly(D-lactide), poly(D,L-lactide), poly(L-lactide-co-D,L-lactide), poly(D-lactide-co-D,L-lactide), poly(L-lactide-co-glycolide), poly(D-lactide-co-glycolide), poly(L-lactide-co-caprolactone), poly(D-lactide-co-caprolactone), poly(L-lactide-co-trimethylene carbonate), poly(D-lactide-co-trimethylene carbonate), poly(D,L-lactide-co-glycolide), poly(D,L-lactide-co-caprolactone), poly(D,L-lactide-co-trimethylene carbonate), a combination thereof, and a blend thereof.

5. The modified polylactide polymer of claim 1, comprising a structure according to the following formula:

$$-\!\!\left[\!\!O\!\!-\!\!\overset{O}{\underset{\|}{C}}\!\!-\!\!\overset{H}{\underset{CH_3}{C}}\right]_{\!\!m}\!\!\!O\!\!-\!\!\overset{O}{\underset{\|}{C}}\!\!-\!\!\overset{CH_2}{\underset{\|}{C}}\!\!-\!\!O\!\!-\!\!\left[\!\!\overset{O}{\underset{\|}{C}}\!\!-\!\!\overset{H}{\underset{CH_3}{C}}\!\!-\!\!O\right]_{\!\!n}\!\!-, \quad \text{(III)}$$

wherein m and n are independently a positive integer.

6. The modified polylactide polymer of claim 1, comprising, in part, a structure according to the following formula:

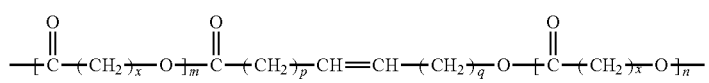

(VIII)

wherein
m and n are independently a positive integer,
x is an integer ranging from 1 to 5 inclusive,
p is an integer ranging from 0 to 3 inclusive, q is an integer ranging from 3 to 0, provided p+q=3.

7. A modified polylactide polymer conjugate produced by reacting the biocompatible functional group of the modified polylactide polymer of claim 1 with a therapeutic agent, a diagnostic agent, a hydrophilic component, a hydrophobic component, or a combination thereof.

8. The modified polylactide polymer conjugate of claim 7, wherein the therapeutic agent is selected from the group consisting of paclitaxel, rapamycin, rapamycin derivative, everolimus, zotarolimus, temsirolimus, deforolimus, merilimus, novolimus, myolimus, umirolimus, biolimus, tacrolimus, pimecrolimus, 16-pent-2-ynyloxy-32(S)-dihydro-rapamycin, and ridaforolimus.

9. The modified polylactide polymer conjugate of claim 7, wherein the diagnostic agent is a radiocontrast agent.

10. The modified polylactide polymer conjugate of claim 7, wherein the hydrophilic component is selected from the group consisting of poly(ethylene glycol) (PEG), a copolymer of PEG, a polymer of hydroxyethyl methacrylate (HEMA), a polymer of hydroxypropyl methacrylate (HPMA), a polymer of hydroxypropyl methacrylamide, a polymer 2-methacryloyloxyethylphosphorylcholine (MPC), a polymer of methacrylic acid (MA), a polymer of acrylic acid (AA), a polymer of alkoxymethacrylate, a polymer of alkoxyacrylate, polymer of 3-trimethylsilylpropyl methacrylate (TMSPMA), a polymer of vinyl alcohol, a polymer of allyl alcohol, a polymer of N-vinyl pyrrolidone (VP), a copolymer of HEMA, a copolymer of HPMA, a copolymer of hydroxypropyl methacrylamide, a copolymer MPC, a copolymer of MA, a copolymer of AA, a copolymer of alkoxymethacrylate, a copolymer of alkoxyacrylate, a copolymer of TMSPMA, a copolymer of vinyl alcohol, a copolymer of allyl alcohol, a copolymer of VP, collagen, chitosan, alginate, fibrin, fibrinogen, cellulose, starch, dextran, dextrin, hyaluronic acid, fragments of hyaluronic acid, derivatives of hyaluronic acid, heparin, fragments of heparin, derivatives of heparin, glycosamino glycan (GAG), GAG derivatives, polysaccharide, elastin, and combinations thereof.

11. The modified polylactide polymer conjugate of claim 7, wherein the hydrophobic component is selected from the group consisting of saturated fatty acids, unsaturated fatty acids, saturated fatty alcohols, unsaturated fatty alcohols, and hydrophobic polymers.

12. A polymer blend comprising the modified polylactide polymer according to claim 1.

13. The polymer blend of claim 12, further comprising poly(L-lactide), poly(L-lactide-co-caprolactone), or a combination thereof.

14. An implantable medical device comprising a device body and optionally a coating, wherein the device body or the coating comprises the modified polylactide polymer according to claim 1.

15. The implantable medical device of claim 14, which is a stent.

16. The implantable medical device of claim 14, which is a bioabsorbable stent.

17. The implantable medical device of claim 14, wherein the device body or the coating further comprises a therapeutic agent.

18. An implantable medical device comprising a device body and optionally a coating, wherein the device body or the coating comprises the modified polylactide polymer conjugate according to claim 7.

19. An implantable medical device comprising a device body and optionally a coating, wherein the device body or the coating comprises the polymer blend according to claim 12.

* * * * *